United States Patent
Slemker et al.

(10) Patent No.: US 7,356,379 B2
(45) Date of Patent: Apr. 8, 2008

(54) METHOD AND ASSOCIATED SYSTEM FOR RECORDING AND RETRIEVING FABRICATION AND/OR FITTING DATA ASSOCIATED WITH A PROSTHETIC COMPONENT

(75) Inventors: Tracy C. Slemker, Clayton, OH (US); Robert Hoskins, Springboro, OH (US); Lucinda Busch, Clayton, OH (US); Scott R. Schall, Clayton, OH (US); Ralph Simmons, Dayton, OH (US)

(73) Assignee: Prosthetic Design, Inc., Clayton, OH (US)

( * ) Notice: Subject to any disclaimer, the term of this patent is extended or adjusted under 35 U.S.C. 154(b) by 0 days.

(21) Appl. No.: 11/288,980

(22) Filed: Nov. 29, 2005

(65) Prior Publication Data

US 2007/0021858 A1    Jan. 25, 2007

Related U.S. Application Data

(63) Continuation-in-part of application No. 11/186,384, filed on Jul. 21, 2005.

(51) Int. Cl.
*G06F 19/00* (2006.01)

(52) U.S. Cl. .................... 700/118; 700/163; 700/182; 623/33; 623/901

(58) Field of Classification Search ............... 700/118, 700/163, 182; 623/33, 36–39, 901; 600/587
See application file for complete search history.

(56) References Cited

U.S. PATENT DOCUMENTS

| | | | |
|---|---|---|---|
| 5,163,965 A | 11/1992 | Rasmusson et al. | |
| 5,339,252 A | 8/1994 | White et al. | |
| 5,432,703 A * | 7/1995 | Clynch et al. | 700/163 |
| 5,824,111 A * | 10/1998 | Schall et al. | 623/33 |
| 5,880,964 A | 3/1999 | Schall et al. | |
| 6,463,351 B1 * | 10/2002 | Clynch | 700/163 |
| 6,470,552 B1 | 10/2002 | Slemker et al. | |
| 6,786,930 B2 * | 9/2004 | Biscup | 623/16.11 |
| 2003/0009354 A1 | 1/2003 | Arbogast et al. | |
| 2004/0133431 A1 | 7/2004 | Udiljak et al. | |
| 2005/0119777 A1 | 6/2005 | Arbogast et al. | |

\* cited by examiner

*Primary Examiner*—Leo Picard
*Assistant Examiner*—Douglas S Lee
(74) *Attorney, Agent, or Firm*—Taft, Stettinius & Hollister LLP

(57) ABSTRACT

A method of socket design and fabrication for Below-the-Knee (BK) amputees that utilizes manual measurements. This method, known as BK by Measurement, utilizes a manual measurement procedure where predetermined points are identified and measurements are taken of a patient's residual limb. These measurements are recorded and thereafter entered into a software package enabling customization by the fabrication facility. Prosthetic components fabricated in accordance with the present invention provide a custom fit, while not relying on more expensive digital imaging technology. The invention also provides a method and associated system for recording and retrieving fabrication and/or fitting data associated with a prosthetic component for use with a particular patient, which can include affixing to the prosthetic component a strip debossed with indicia unique to the particular patient or prosthetic component.

5 Claims, 25 Drawing Sheets

(a)

(b)

(c)

(a)  (b)

(c)

(a)

(b)

(c)

METHOD AND ASSOCIATED SYSTEM FOR RECORDING AND RETRIEVING FABRICATION AND/OR FITTING DATA ASSOCIATED WITH A PROSTHETIC COMPONENT

CROSS-REFERENCE TO RELATED APPLICATION

This application is a continuation-in-part of U.S. patent application Ser. No. 11/186,384, filed Jul. 21, 2005, the disclosure of which is incorporated herein by reference.

BACKGROUND

Starting in the early 1990s, many Orthotic and Prosthetic (O&P) care professionals saw trends that pointed to a rapid increase in the population of amputees due mainly to longer life spans of existing amputees and an increasing number of people facing risk factors that lead to amputations. Those trends led to the desire for computer-aided design and manufacturing (CAD/CAM) to help the practitioners reduce time spent on patient care, while increasing the quality of that care. Before CAD/CAM became commonplace in the industry, practitioners relied on labor-intensive methods involving plaster casts and heavy plaster models that resulted in patients often waiting weeks for new sockets.

Vendors providing CAD/CAM worked with practitioners to develop effective systems and methods for socket sizing. Popular CAD software available today requires the use of scanning devices to digitize patient residual limb dimensions. These devices include rotating digitizers, tactile tracing pens, laser scanners, and digital cameras. Such devices, while often creating a highly accurate digital representation of the residual limb, could potentially create errors undetectable and out of the control of the practitioner. In addition, the costs involved with using CAD devices are often prohibitive, especially when calculating the high costs in dollars and time spent learning the CAD design techniques.

Thus, there is a need in the art to provide lower cost alternatives to prosthesis fitting practitioners, while continuing to utilize software in designing prosthetic components to be custom fabricated. This need, along with others, is satisfied by the present invention.

SUMMARY

It is a first aspect of the present invention to provide a method of socket design and fabrication for Below-the-Knee (BK) amputees that utilizes manual measurements. This method, known as BK by Measurement, utilizes a manual measurement procedure where predetermined points are identified and measurements are taken of a patient's residual limb. These measurements are recorded and thereafter entered into a software package enabling customization by the fabrication facility. Prosthetic components fabricated in accordance with the present invention provide a custom fit, while not relying on more expensive digital imaging technology.

It is a second aspect of the present invention to provide a method and associated system for recording and retrieving fabrication and/or fitting data associated with a prosthetic component for use with a particular patient and; more specifically, to a method and associated system associating a unique indicia with a patient's prosthetic component that allows for identification and retrieval of the fabrication and/or fitting data associated with a prosthetic component, so as to facilitate manufacturing and/or fitting a new prosthetic component for the patient.

An exemplary debossing procedure according to the second aspect of the present invention includes debossing an aluminum labeling strip (0.5×4 inches) using the Imperial Regal electric nameplate machine with a 0.1875 letter embossing wheel. Four sheets of backing paper are positioned under the spring loaded clamp of the nameplate machine. The aluminum strip is mounted to the paper by using tape at each end of the strip. The aluminum strip is aligned under the wheel and, using keyboard of the nameplate machine, the patient's name and other unique indicia are debossed onto the strip. After completion of debossing the unique indicia onto the strip, the strip is removed from the nameplate machine and attached to block using double sided tape, with the embossed raised indicia opposite the block. Subsequent to the material of the prosthetic component being sufficiently soft, the embossed side of the strip is pushed into the prosthetic component using the block to create a debossed impression of the unique indicia, where the block is optionally pressed into the component in a rolling manner where the surface of the prosthetic component is arcuate. After the prosthetic component has cooled to impart a sufficient degree of rigidity to the debossed unique indicia, a paint tip marker is used to highlight the debossed indicia. Alternatively, a large tip marker may be utilized, with the excess paint being removed by using a towel or other wiping material.

DETAILED DESCRIPTION

It should be understood that the following detailed description of embodiments of the present invention are exemplary in nature and are not intended to constitute limitations upon the present invention. It is also to be understood that variations of the exemplary embodiments contemplated by one of ordinary skill in the art shall concurrently fall within the scope and spirit of the invention.

Figure 24:
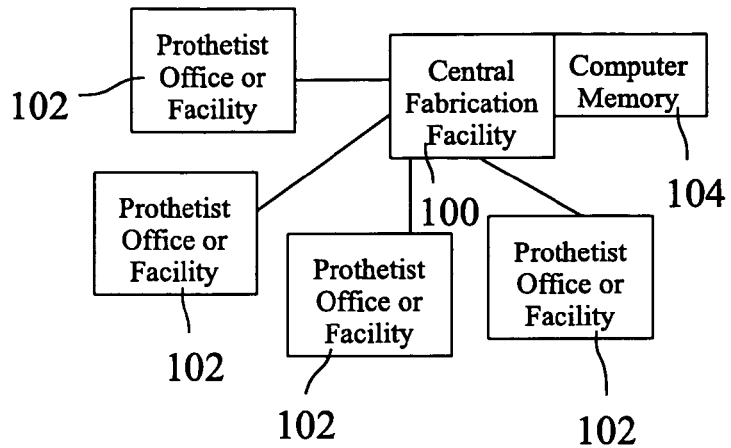
FIG. 24 is a schematic diagram of communication between a central fabrication facility and a plurality of prosthetist facilities in accordance with the present invention.

As shown in FIG. 24, the exemplary embodiments of the present invention may utilize a business model for the fabrication and fitting of prosthetic limbs and prosthetic limb components involving a central fabrication facility 100 and plurality of remote prosthetist offices or facilities 102. The central fabrication facility 100 is able to communicate electronically to each of the remote offices (and vice versa) through a data link such as the Internet. In this model the central fabrication facility 100 has equipment, such as carvers and thermoformers for fabricating certain prosthetic limb components, such as prosthetic limb socket components, while the remote prosthetist offices 102 are conveniently located for patient visits and include people and equipment for collecting data from the patient necessary for the central fabrication facility to fabricate the prosthetic limb or prosthetic limb component therefrom.

Figure 25:
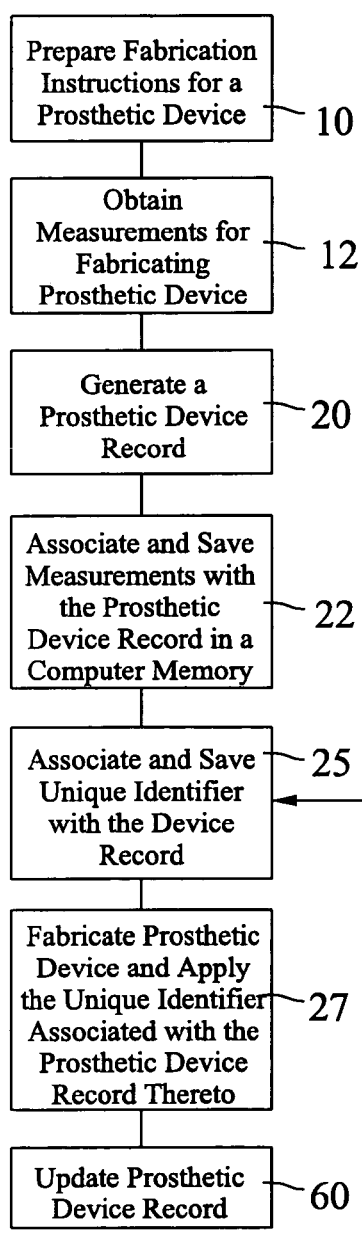
FIG. 25 is an exemplary flow diagram in accordance with the present invention.

Referencing FIGS. 24 and 25, the present invention includes a method and associated devices for including a unique identifier associating a prosthetic component with a specific patient. Such a method includes the step 10 of preparing fabrication and/or fitting data for a customized prosthetic device. In the exemplary embodiment this data is prepared at a remote prosthetist office 102 and transmitted to the central fabrication facility 100 over the data link. Customized prosthetic devices include, but are not limited to, upper leg sockets, lower leg sockets, upper arm sockets, and lower arm sockets. Such fabrication and/or fitting data may include dimensions of the patient's residual limb, orientation and/or position data of prosthetic limb components, materials information, component identifications, adjustment data, and the like. In the exemplary embodiment the step 10 may include the step 12 of obtaining profile data, including residual limb dimensions and associated modifications (which can include the BK by Measurement profile data submitted by the remote facility 102), necessary to fabricate an upper leg socket of a prosthetic limb. The BK by Measurement process is described below.

An embodiment of present invention is directed to a method of socket design for Below-the-Knee (BK) amputees that utilizes manual measurements. This method, known as BK by Measurement, utilizes a manual measurement procedure where predetermined points are identified and measurements are taken of a patient's residual limb at a remote facility 102. These measurements are recorded and thereafter entered into a software package enabling customization by the central fabrication facility 100. Prosthetic components fabricated in accordance with the present invention provide a custom fit, while not relying on more expensive digital imaging technology.

Figure 3:
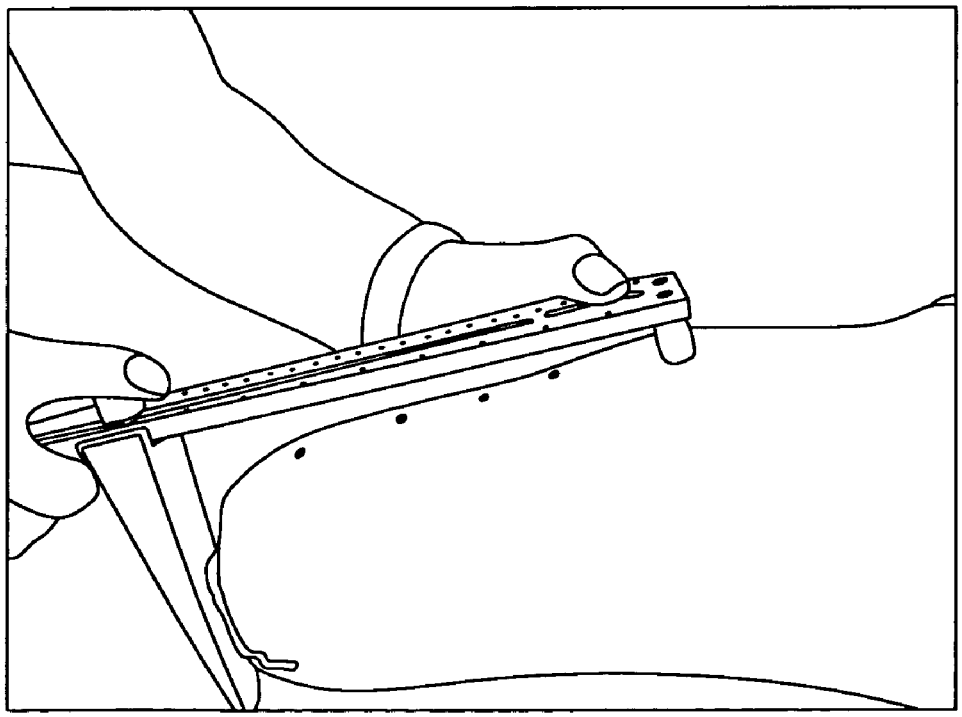
FIG. 3 is an exemplary photograph showing a measurement taken of an amputee's residual limb from the knee center to the distal end in accordance with the present invention.
Figure 4:
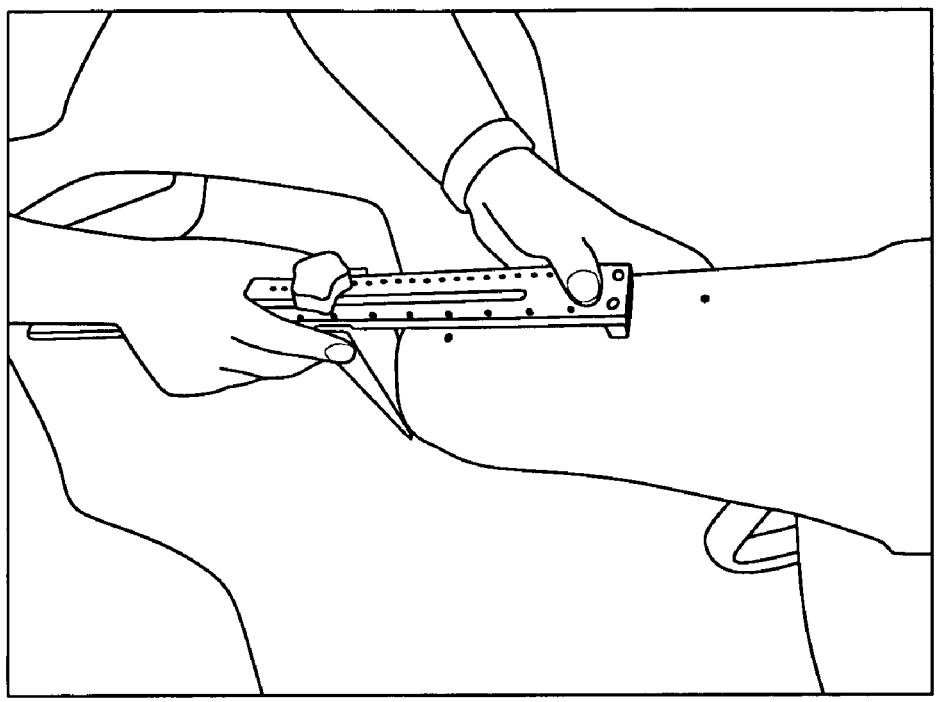
FIG. 4 is an exemplary photograph showing a measurement taken of an amputee's residual limb from the mid patella tendon to the distal end in accordance with the present invention.
Figure 5:
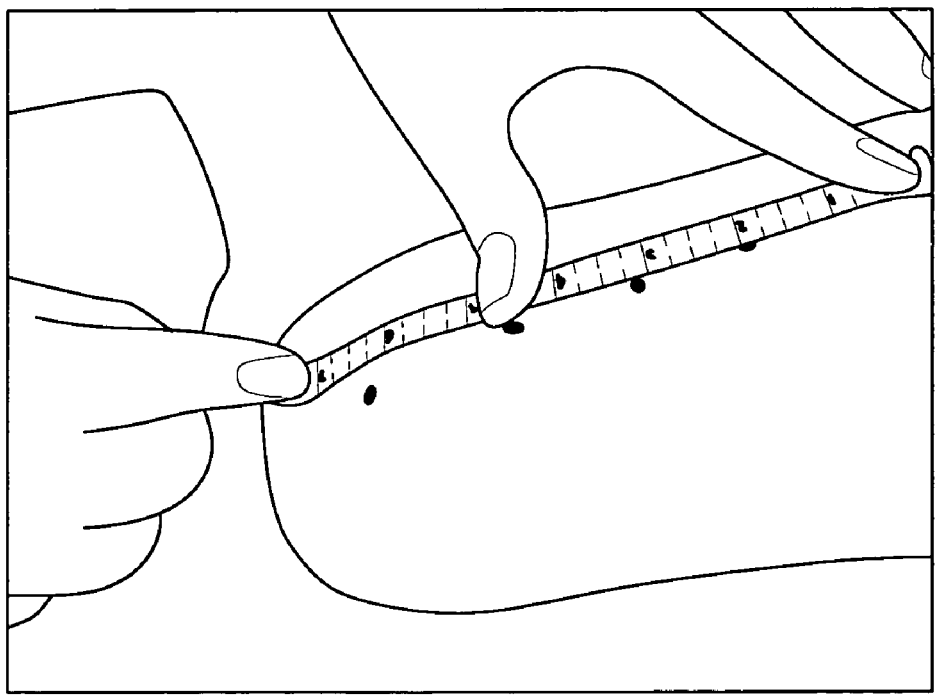
FIG. 5 is an exemplary photograph showing a measurement taken of an amputee's residual limb from the knee center to other landmarks in accordance with the present invention.
Figure 6:
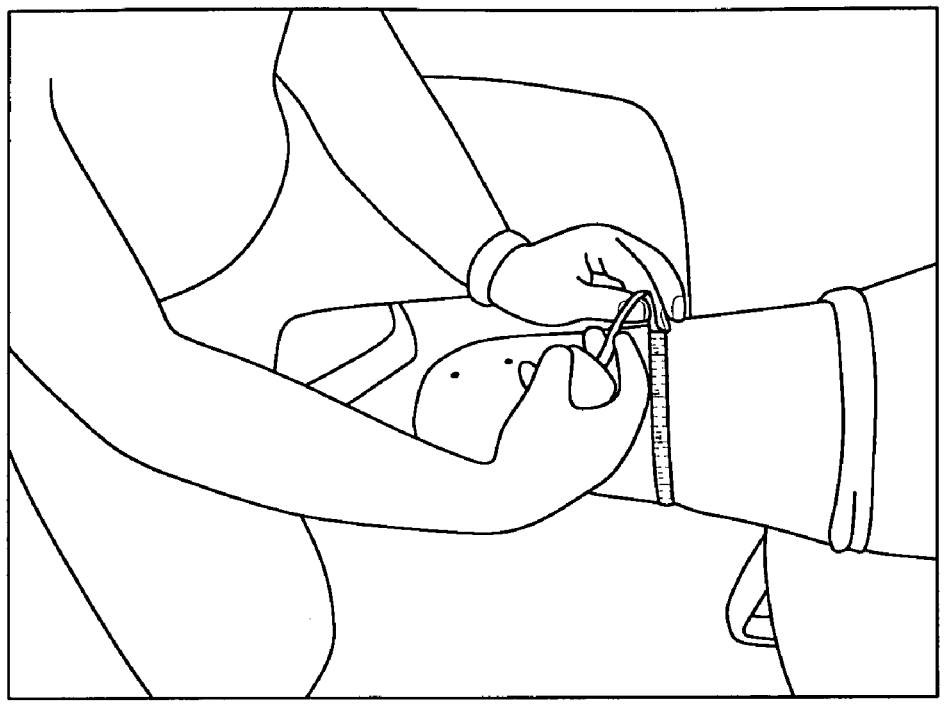
FIG. 6 is an exemplary photograph showing a circumferential measurement taken of an amputee's residual limb in accordance with the present invention.
Figure 7:
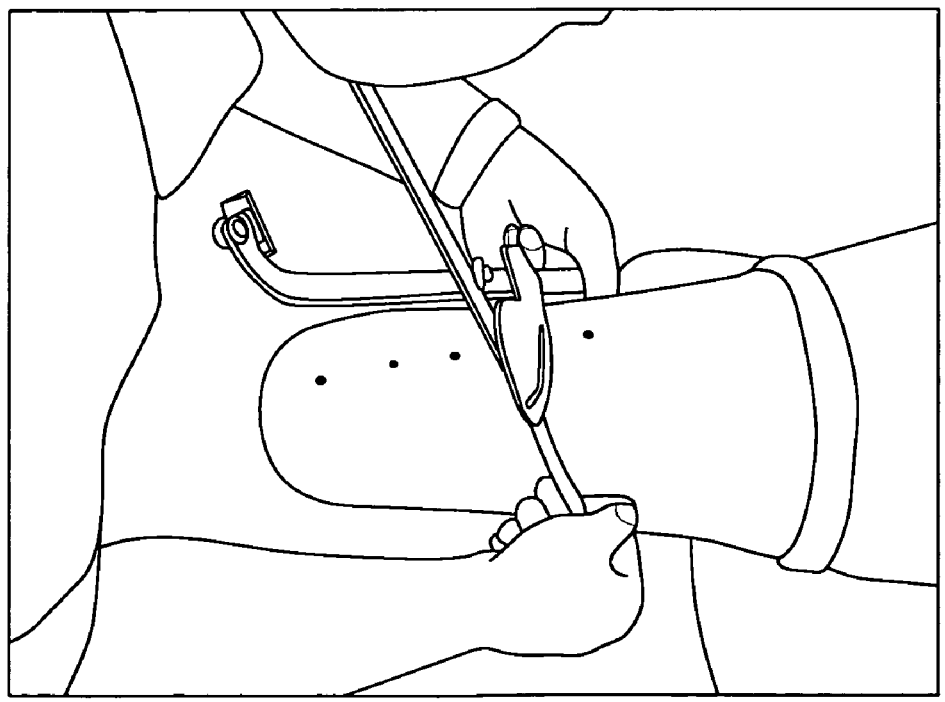
FIG. 7 is an exemplary photograph showing a medial to lateral measurement taken of an amputee's residual limb at the knee center in accordance with the present invention.
Figure 8:
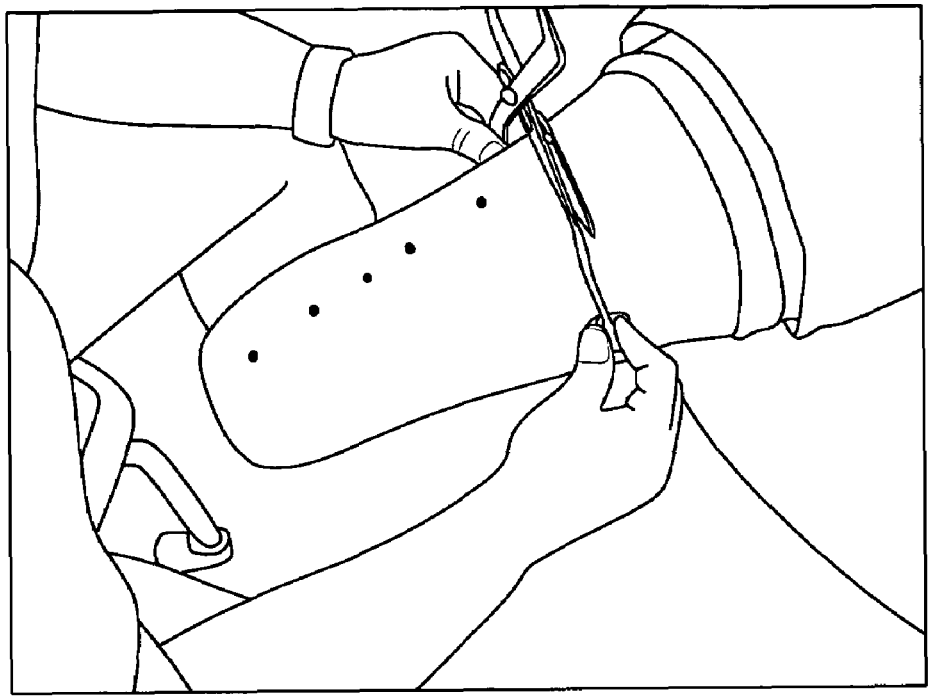
FIG. 8 is an exemplary photograph showing a proximal medial to lateral measurement taken of an amputee's residual limb in accordance with the present invention.
Figure 9:
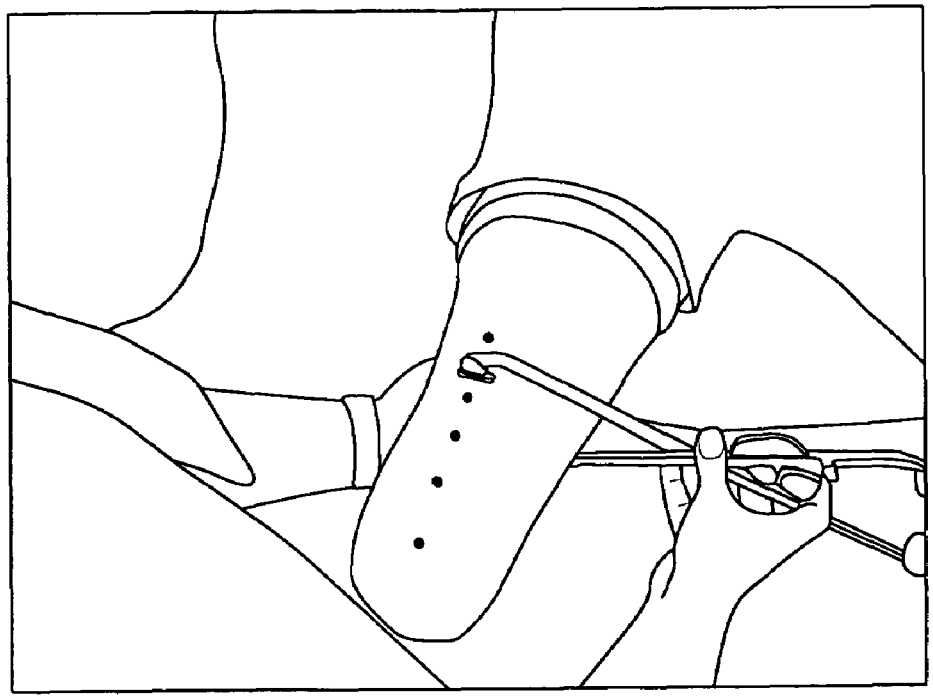
FIG. 9 is an exemplary photograph showing an anterior to posterior measurement taken of an amputee's residual limb at the mid patella tendon in accordance with the present invention.
Figure 10:
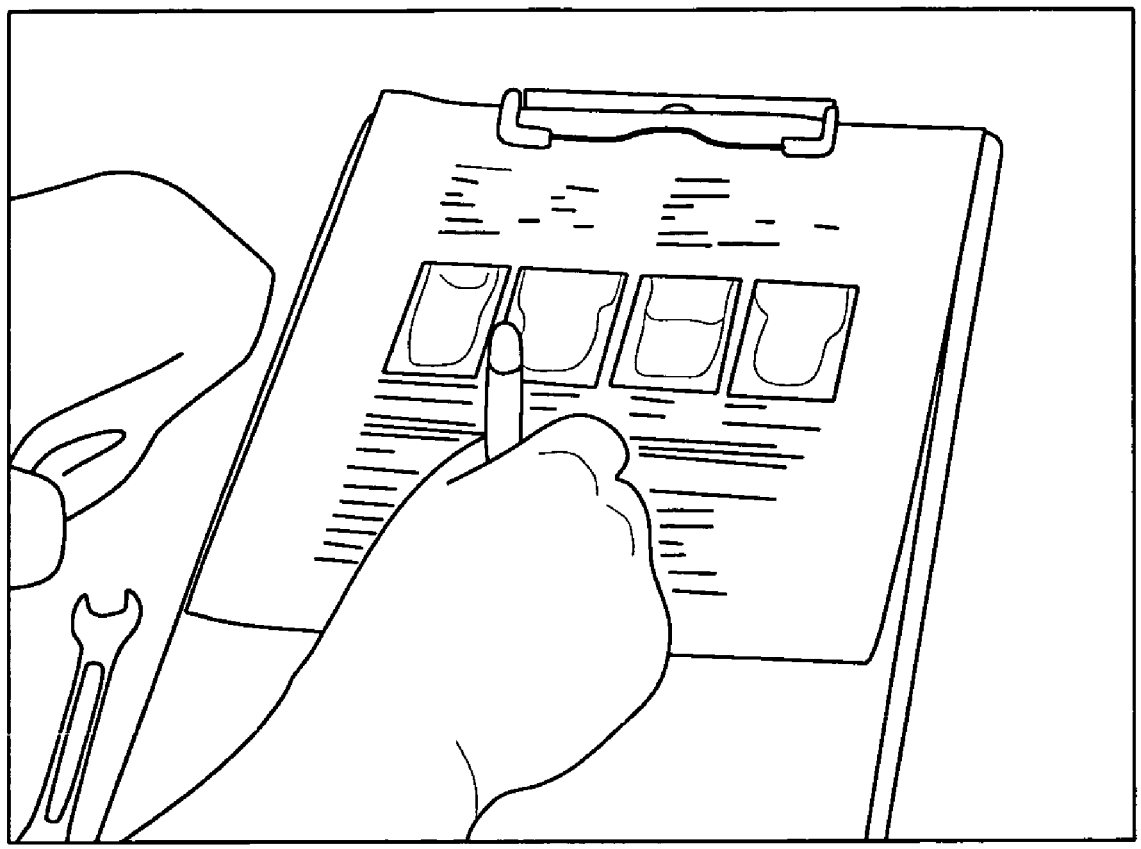
FIG. 10 is an exemplary photograph showing recordation of measurements taken of an amputee's residual limb onto an exemplary transtibial measurement chart in accordance with the present invention.

An exemplary embodiment of the BK by Measurement process proceeds as follows. Referencing FIGS. 1-10, the following landmarks of the patient's residual limb are identified and marked (See FIG. 2): knee center; mid patella tendon; tibial tuberosity; distal tibia; and, demarcation to include locking the liner "basket". Thereafter, a sequence of measurements is taken and recorded (See FIGS. 1 and 10) that include: a straight line length measurement from the knee center to the distal end of the residual limb (See FIG. 3); a straight line length measurement from the mid patella tendon to the distal end of the residual limb (See FIG. 4); a series of accurate line length measurements from the knee center to the mid patella tendon, the tibial tuberosity, and the distal tibia (these measurements may be taken using a tape measure) (See FIG. 5); a series of circumferential measurements are taken at the knee center, the mid patella tendon, the tibial tuberosity, and the distal tibia (See FIG. 6); a medial-to-lateral measurement (width) at the knee center (See FIG. 7); a medial-to-lateral measurement on the proximal side of the knee center (See FIG. 8); and, an anterior-to-posterior measurement (width) at the mid patella tendon (See FIG. 9). The recorded measurements (see FIGS. 1 and 10) are then forwarded to the central fabrication facility 100 for use with fabricating a three-dimensional representation of the patient's residual limb and thereafter the prosthetic socket corresponding to the patient's residual limb.

Figure 11:
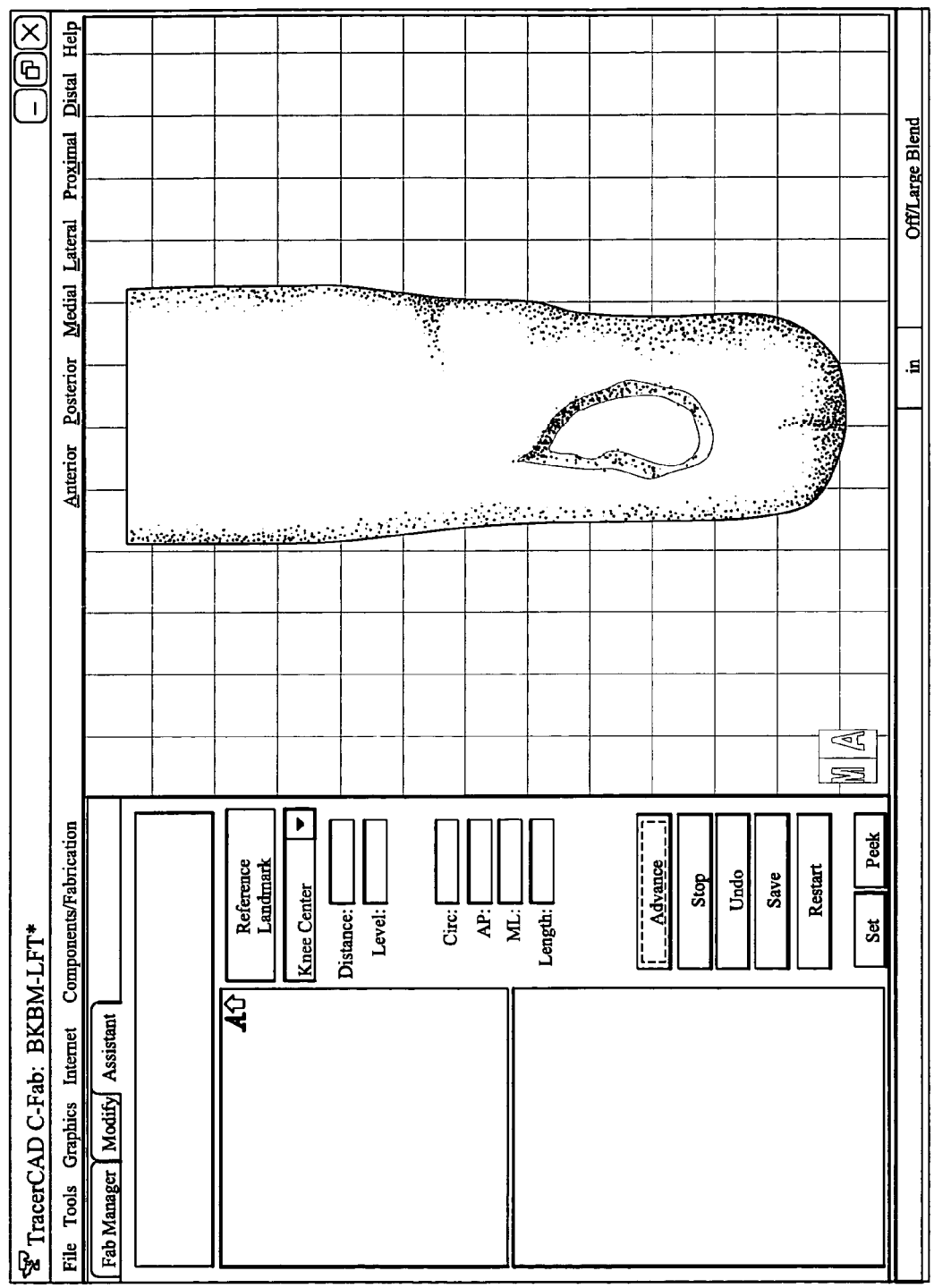
FIG. 11 is an exemplary screenshot and associated overview directions for using a software program called TracerCAD in accordance with the present invention.

Referencing FIG. 11, an exemplary software package that may be utilized with the present invention is TracerCAD commercially available from Tracer, 20283 State Road 7, Suite 219, Boca Raton, Fla. 33498 (www.tracercad.com). Those of ordinary skill will readily understand that other software packages may be used with the present invention, however, for those skilled in the art that may want to use TracerCAD; the following is a brief summary of some of the features of TracerCAD.

TracerCAD is a program designed for custom modification of prosthetic device designs prior to fabrication. Drawing on TracerCAD is accomplished by holding down the left mouse button, while the blending feature is accomplished holding down the right mouse button on a dual button peripheral. Current versions of TracerCAD include three operational modes: Fab Manager; Modify; and, Assistant. Users may select from six different views to include anterior, posterior, medial, lateral, proximal, and distal. TracerCAD also makes use of audible prompts and, therefore, it is helpful to provide an audio outlet during use of TracerCAD. It should be noted that in the Figures referenced below, text appearing in BOLD on the Figures corresponds to an audible prompt of TracerCAD.

Figure 12:
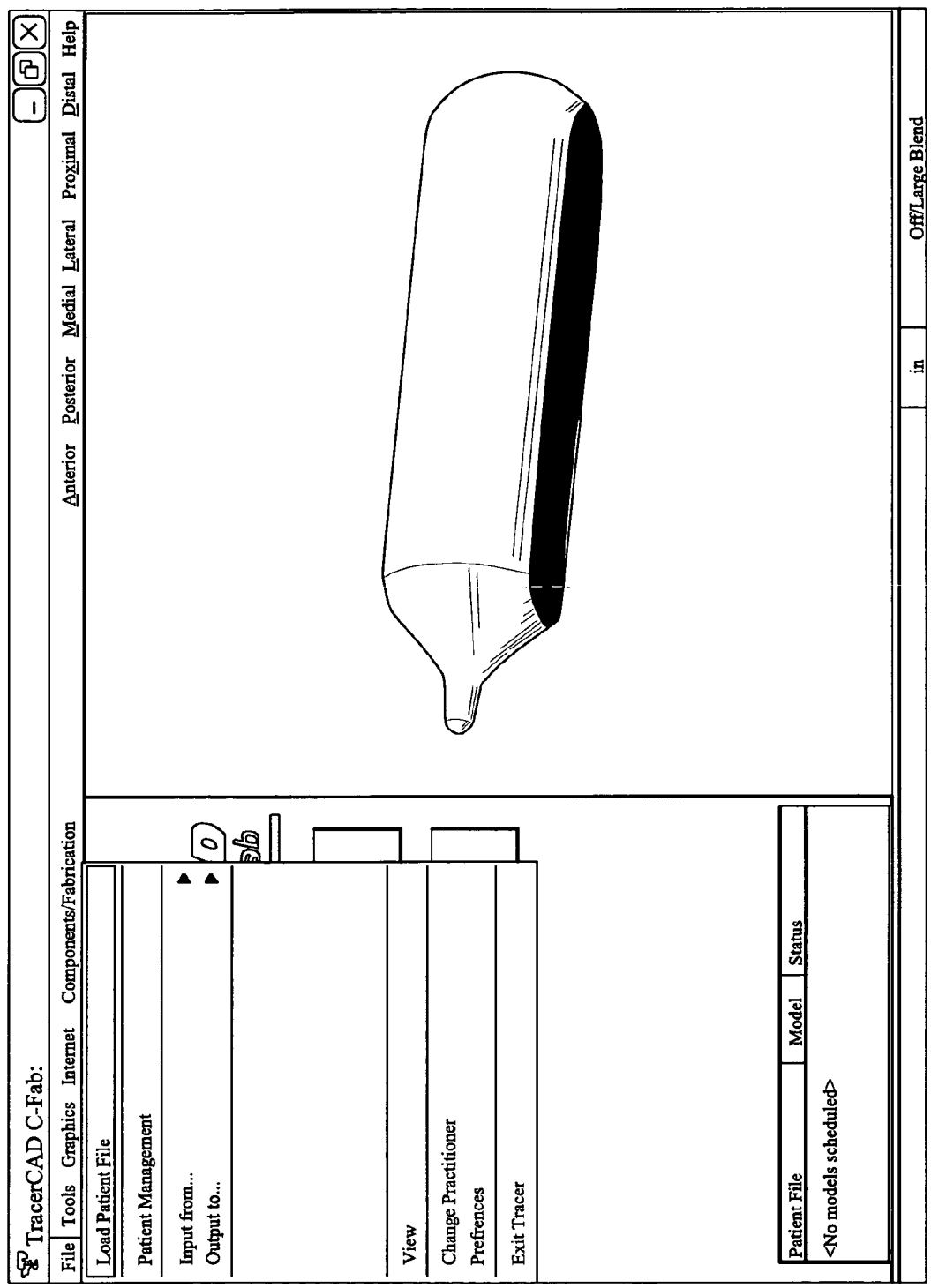
FIG. 12 is an exemplary screenshot of a starting template provided by TracerCAD, along with exemplary steps to follow to modify the template in accordance with the present invention.

Referring to FIG. 12, the TracerCAD program is activated and a patient file previously stored on the central fabrication facility's database is selected by clicking on the "File" menu and selecting "Load Patient File". In exemplary form, the patient file for purposes of discussion has been saved and named as "BMBK-LFT/RT". It is also within the scope of the invention that the patient file be newly generated, as shown in step 4, and include the entry of patient information as well as any comment provided by the measuring clinician.

Figure 13:
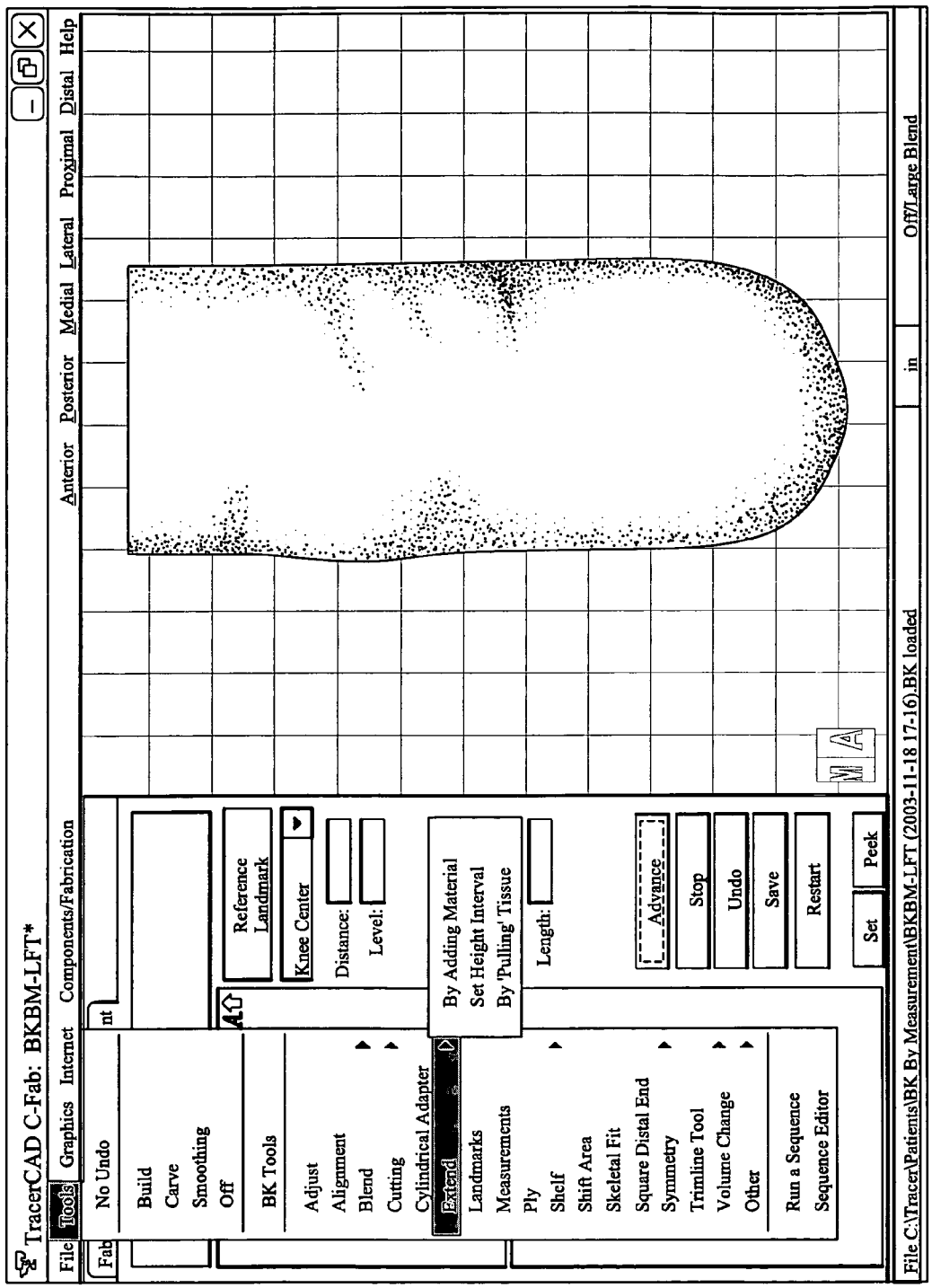
FIG. 13 is an exemplary screenshot of an electronic representation of a below knee residual limb of an amputee, along with exemplary steps to follow in accordance with the present invention.

Referring to FIG. 13, TracerCAD starts off by providing a stock prosthetic socket for below-the-knee (BK) applications. The stock socket will be manipulated according to the measurements taken such as, without limitation, those recorded in FIG. 1. One such manipulation may include modifying the length from the knee center to the distal end of the patient's residual limb. In exemplary form, this process may include activating the "Assistant" tab, activating the "Tools" menu, selecting the option "Extend", and finally selecting the "By Adding Material" option. The resulting prompt requests an input of a numerical value to lengthen or shorten the socket, where negative numbers will shorten the socket and positive numbers will lengthen the socket. TracerCAD, however, needs to know the points of reference and a user may identify such points of reference for TracerCAD by utilizing the cursor to click on the knee center and distal end provide two such exemplary reference points. To confirm that the length agrees with the values entered by the clinician, an "Anterior" view may be selected. If the length is not proper, the above steps may be repeated until the desired length is achieved.

Figure 14:
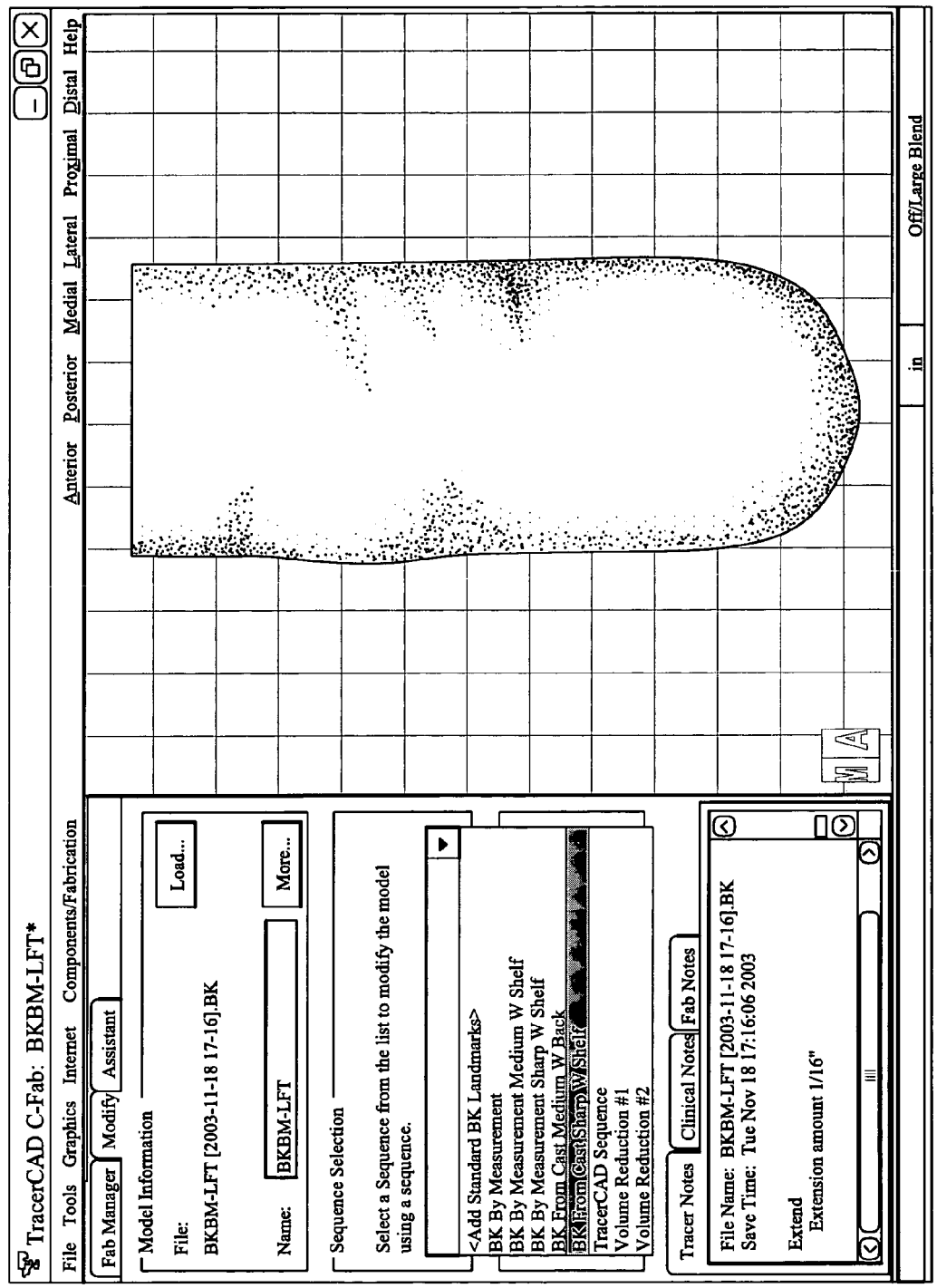
FIG. 14 is an exemplary screenshot of the electronic representation of FIG. 13, along with exemplary steps to follow in accordance with the present invention.

Referencing FIG. 14, TracerCAD includes a feature known as "Sequence Editor." A sequence in TracerCAD is a series of clinical steps that guide the user through the modification of a prosthetic design model. Sequences allow a user to program TracerCAD to follow a series of steps once, and then execute those steps repeatedly in series. Sequence Editor is a customizable feature that requires inputting of information as to the measurements that TracerCAD will prompt a user for, as well as the order that the prompts for measurements are displayed/signaled to the user. Users of TracerCAD can create, modify, or remove sequences and those of ordinary skill are familiar with such techniques. The following discussion includes a custom sequence developed in accordance with the present invention hereafter referred to as "BK by Measurement with Sharp W Shelf." Clicking on the Modify Tab enables selection of the sequence "BK by Measurement with Sharp W Shelf."

Figure 15:
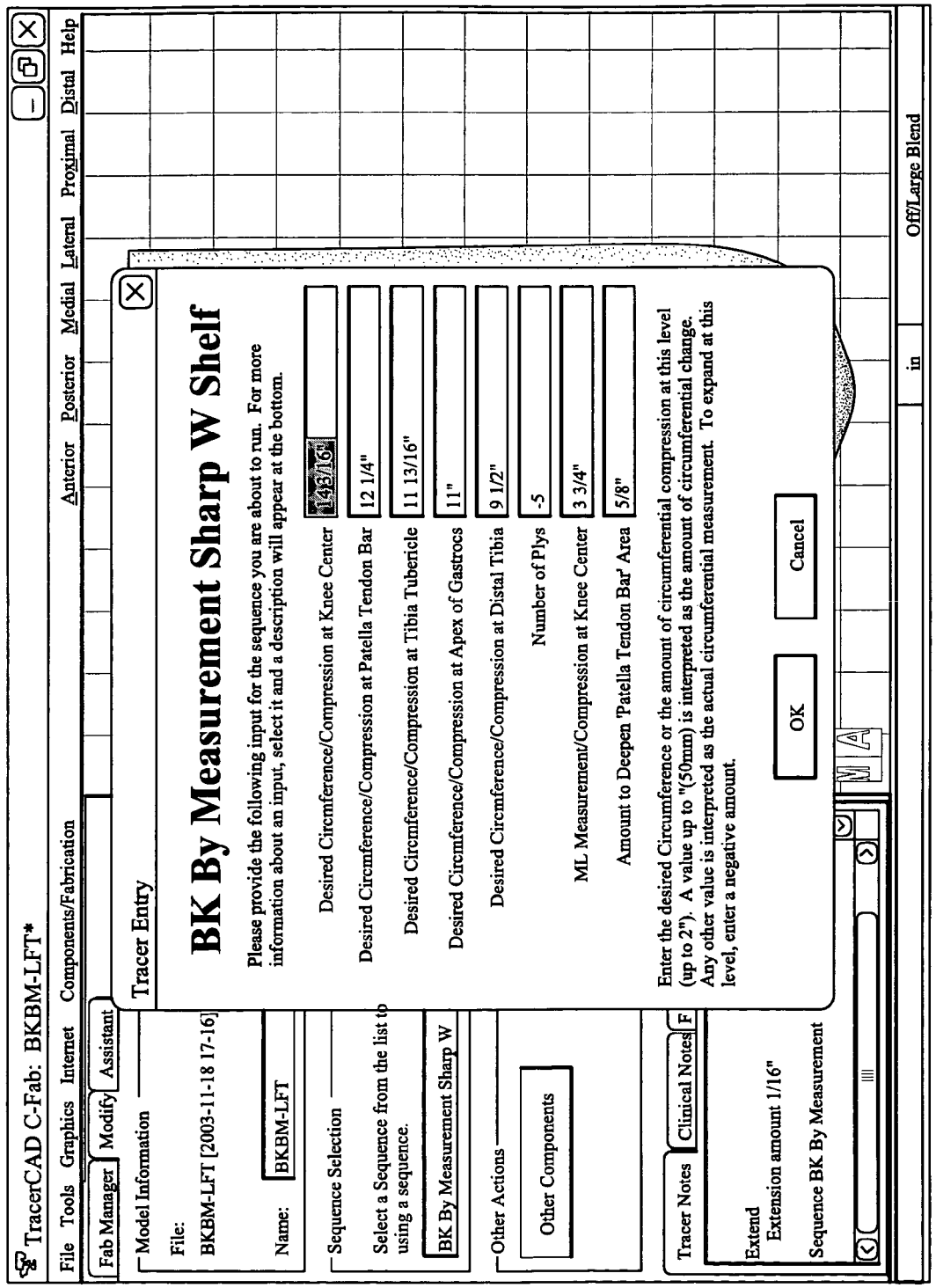
FIG. 15 is an exemplary screenshot of a first aspect of a custom sequence having measurement data inputs, as well as exemplary steps to follow to input such measurements in accordance with the present invention.

As shown in FIG. 15, the "BK by Measurement with Sharp W Shelf" sequence prompts a user to input a series of measurements taken from a residual limb of a patient. The prompt includes inputs for: (1) desired circumference/compression at the knee center; (2) desired circumference/compression at the patella tendon bar; (3) desired circumference/compression at the tibia tubercle; (4) desired circumference/compression at the apex of gastrocs; (5) desired circumference/compression at the distal tibia; (6) number of ply; (7) medial/lateral measurement/compression at the knee center; and (8) amount to deepen the patella tendon bar. It is to be understood that the entry of data in this particular window is not required to be inputted in the order recited above. After the data is inputted, the "OK" button is clicked to go to the next measurement input window.

Figure 16:
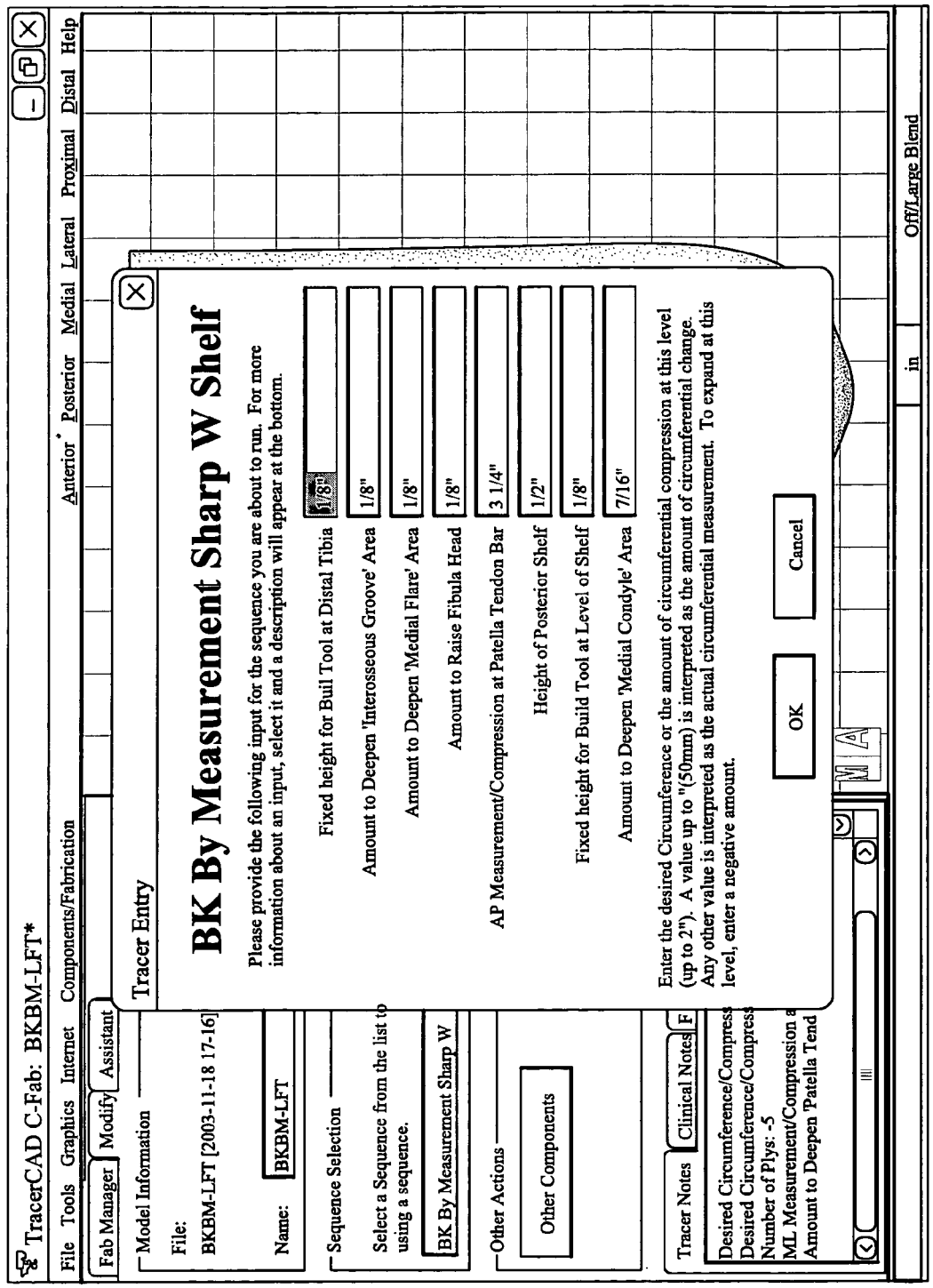
FIG. 16 is an exemplary screenshot of a second aspect of the custom sequence having measurement data inputs, as well as exemplary steps to follow to input such measurements in accordance with the present invention.

Referencing FIG. 16, the "BK by Measurement with Sharp W Shelf" sequence prompts a user to input additional measurements taken from the residual limb of the patient. In addition to the particular measurements prompted by the "BK by Measurement with Sharp W Shelf," the sequence also has defined the range of measurements that will be accepted as a proper data entry. The following data entry descriptions for this window are recited, followed by the range of measurements acceptable for entry. The prompt includes inputs for: (1) fixed height for build tool at distal tibia ($1/8"-3/16"$); (2) amount to deepen interosseous groove area ($1/8"-3/16"$); (3) amount to deepen medial flare area ($1/8"-3/16"$); (4) amount to raise fibula head ($1/8"-3/16"$); (5) anterior/posterior measurement/compression at the patella tendon bar; (6) height of posterior shelf ($1/2"-3/4"$); (7) fixed height of build tool as level of shelf; and (8) amount to deepen the medial condyle. It is to be understood that the entry of data in this particular window is not required to be inputted in the order recited above. After the data is inputted, the "OK" button is clicked to go to the next input window.

Figure 1:
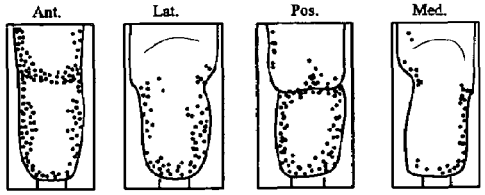
FIG. 1 is an exemplary transtibial measurement chart for use with the present invention.
Figure 17:
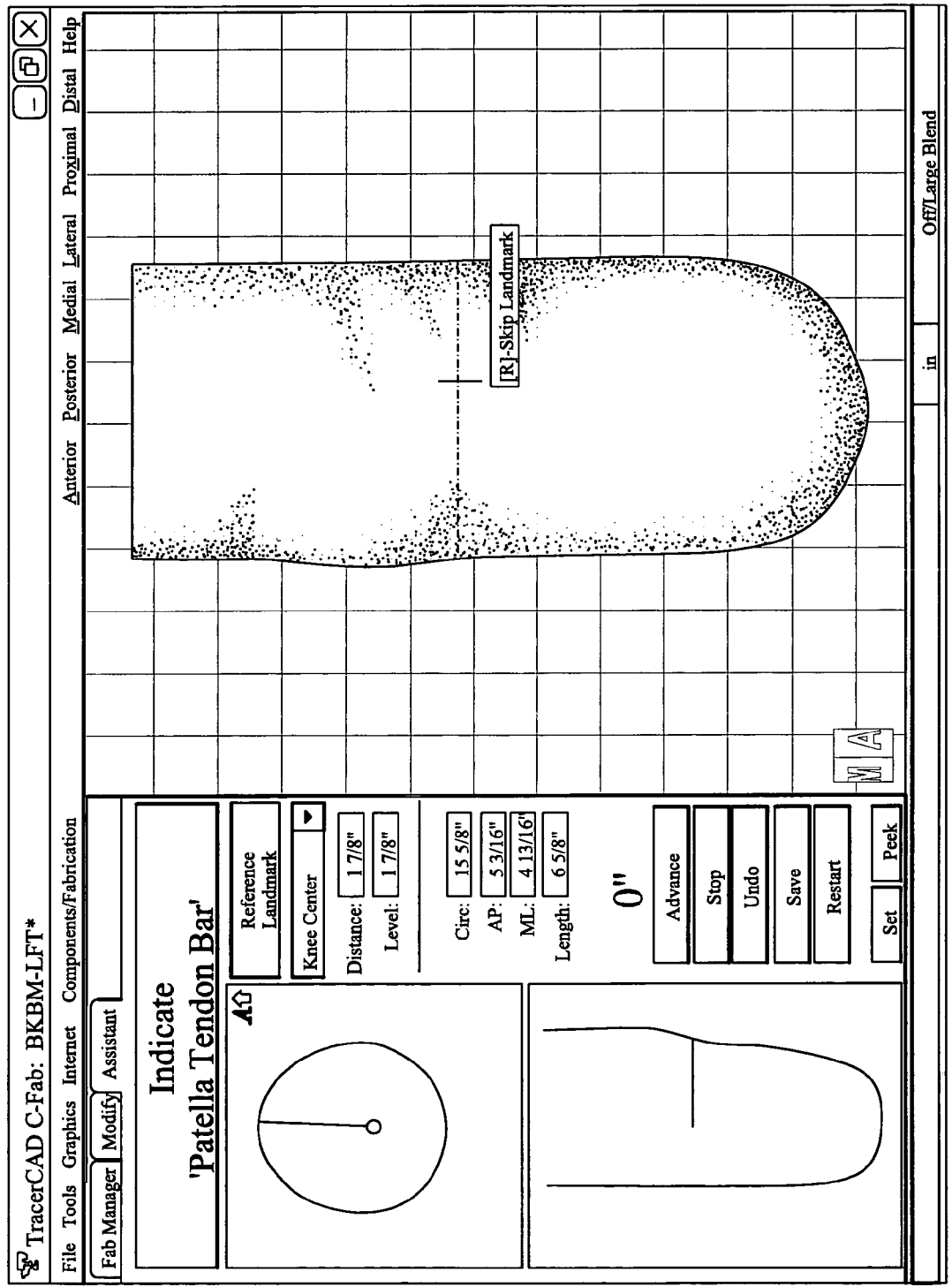
FIG. 17 is an exemplary screenshot of the electronic representation of the below knee residual limb based upon the data input into the custom sequence as shown in exemplary form in FIGS. 15 and 16, as well as an overview of exemplary steps to define landmarks on the electronic representation of the amputee's residual limb in accordance with the present invention.
Figure 18:
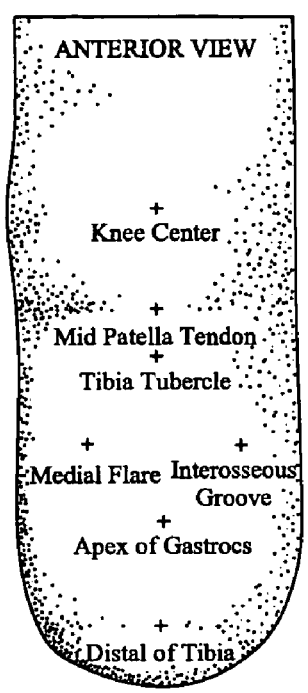
FIG. 18 includes three exemplary screenshots showing anterior, lateral, and medial views of the electronic representation of the below knee residual limb that includes a series of landmark labels, as well as exemplary steps and instructions to follow to locate and label the landmarks in accordance with the present invention.
Figure 18:
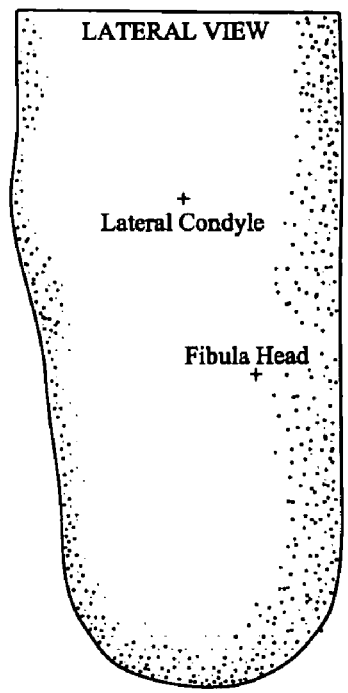
Figure 18:
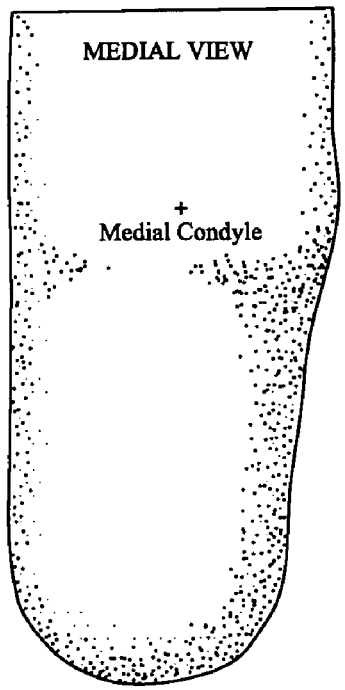
Figure 19:
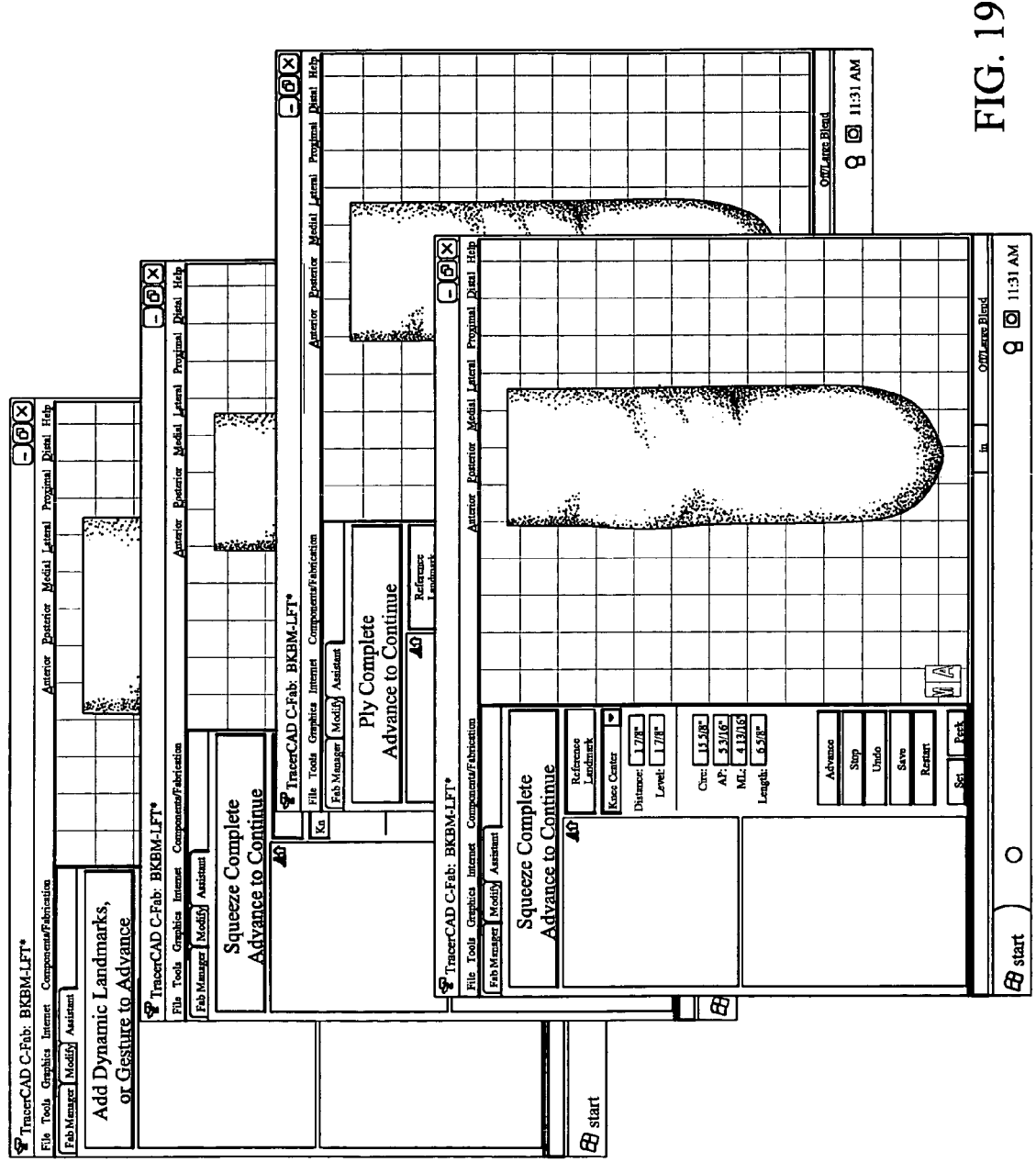
FIG. 19 includes a series of staggered screenshots showing a series of prompts that automatically adjust for circumference, ply, and squeeze of the electronic representation of the below knee residual limb based upon the measurement inputs as shown in FIGS. 15 and 16, as well as an overview to later steps in the sequence that may involve building, drawing, carving, and blending in accordance with the present invention.
Figure 20:
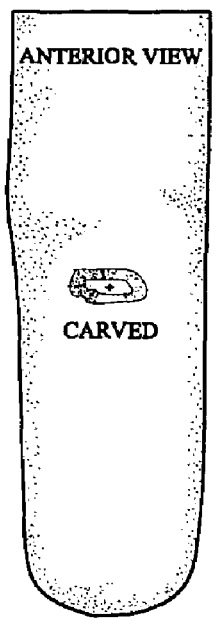
FIG. 20 includes three exemplary screenshots showing the patella tendon bar, the tibial crest, and interosseous groove of the electronic representation of the below knee residual limb, each being carved or built and thereafter blended, as well as exemplary steps and instructions to follow in accordance with the present invention.
Figure 20:
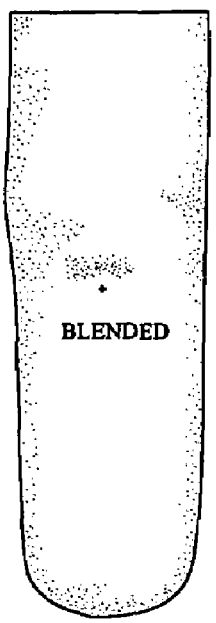
Figure 20:
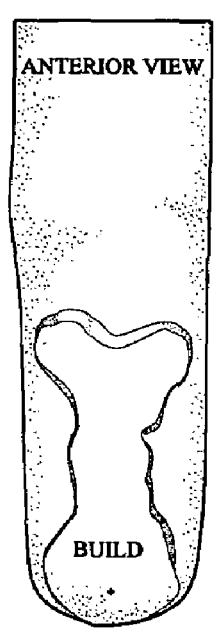
Figure 20:
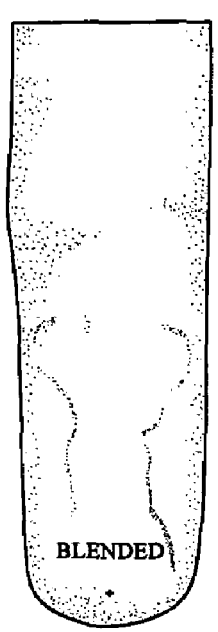
Figure 20:
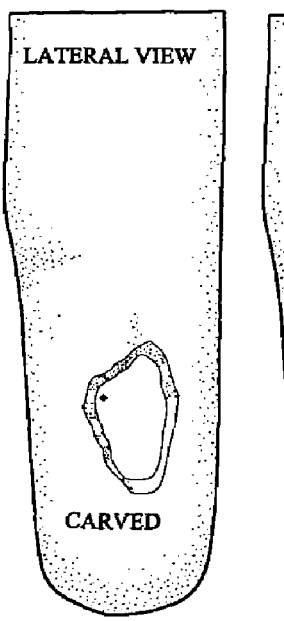
Figure 20:
Figure 21:
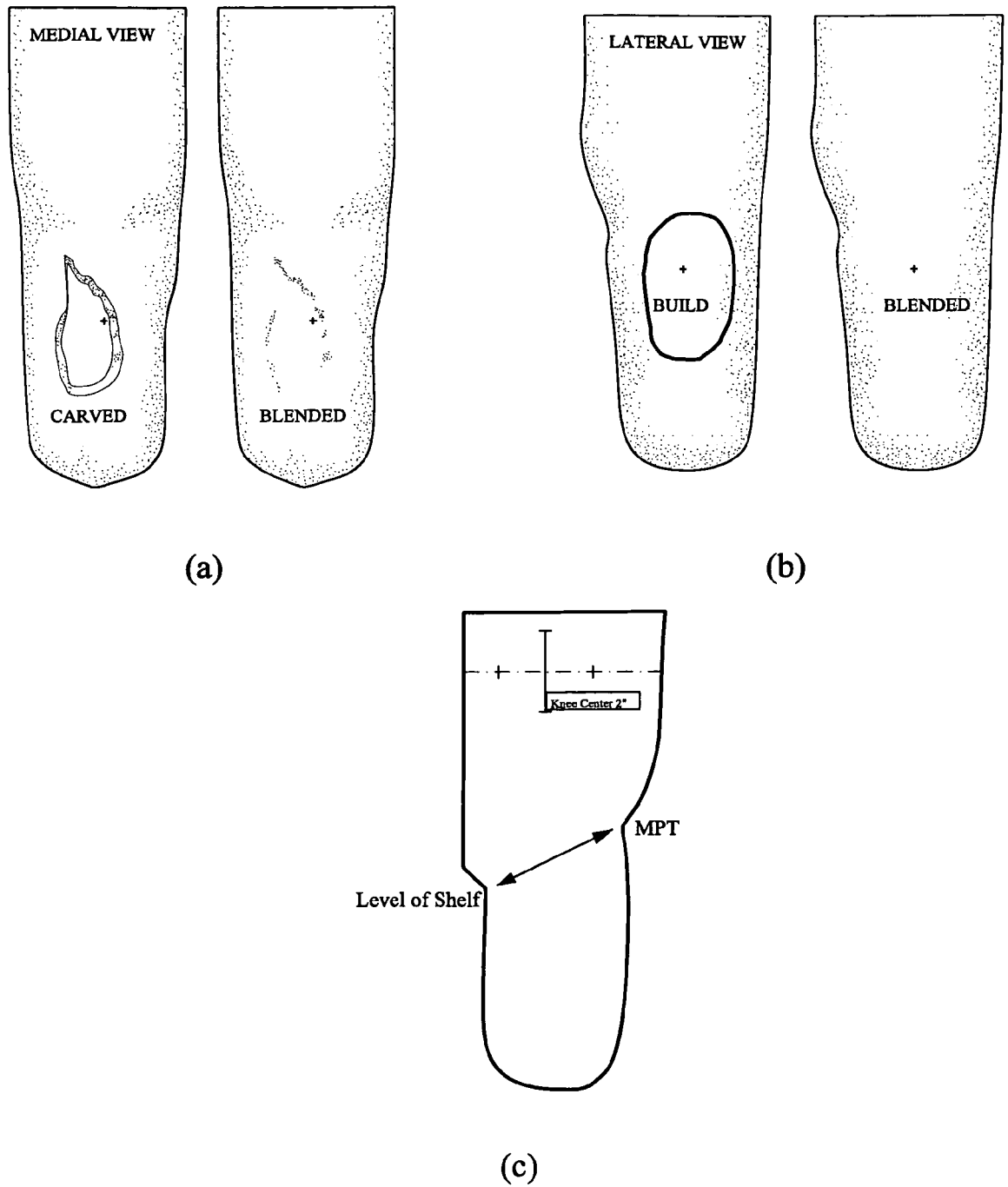
FIG. 21 includes three exemplary screenshots showing the medial flare, the fibula head, and the level of the shelf of the electronic representation of the below knee residual limb, as well as exemplary steps and instructions to follow in accordance with the present invention.
Figure 22:
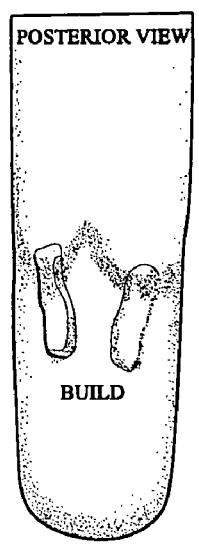
FIG. 22 includes three exemplary screenshots showing the posterior view of the shelf, the medial condyle, and the lateral condyle of the electronic representation of the below knee residual limb, each being carved or built and thereafter blended, as well as exemplary steps and instructions to follow in accordance with the present invention.
Figure 22:
Figure 22:
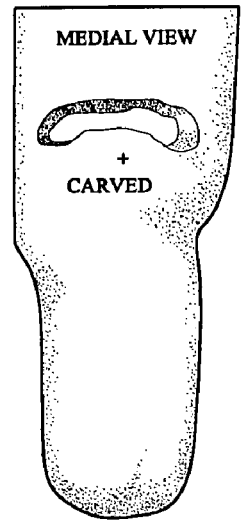
Figure 22:
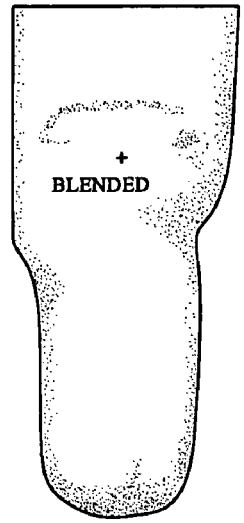
Figure 22:
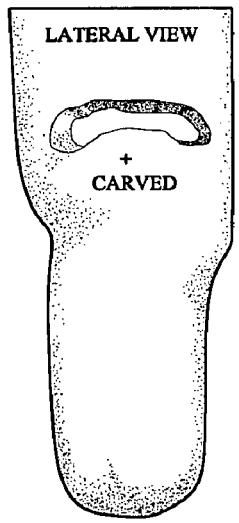
Figure 22:
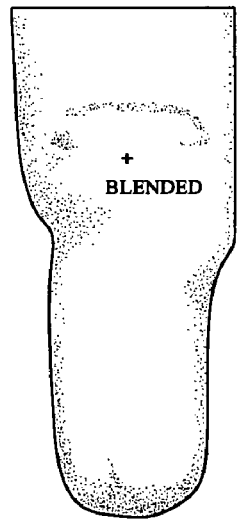
Figure 23:
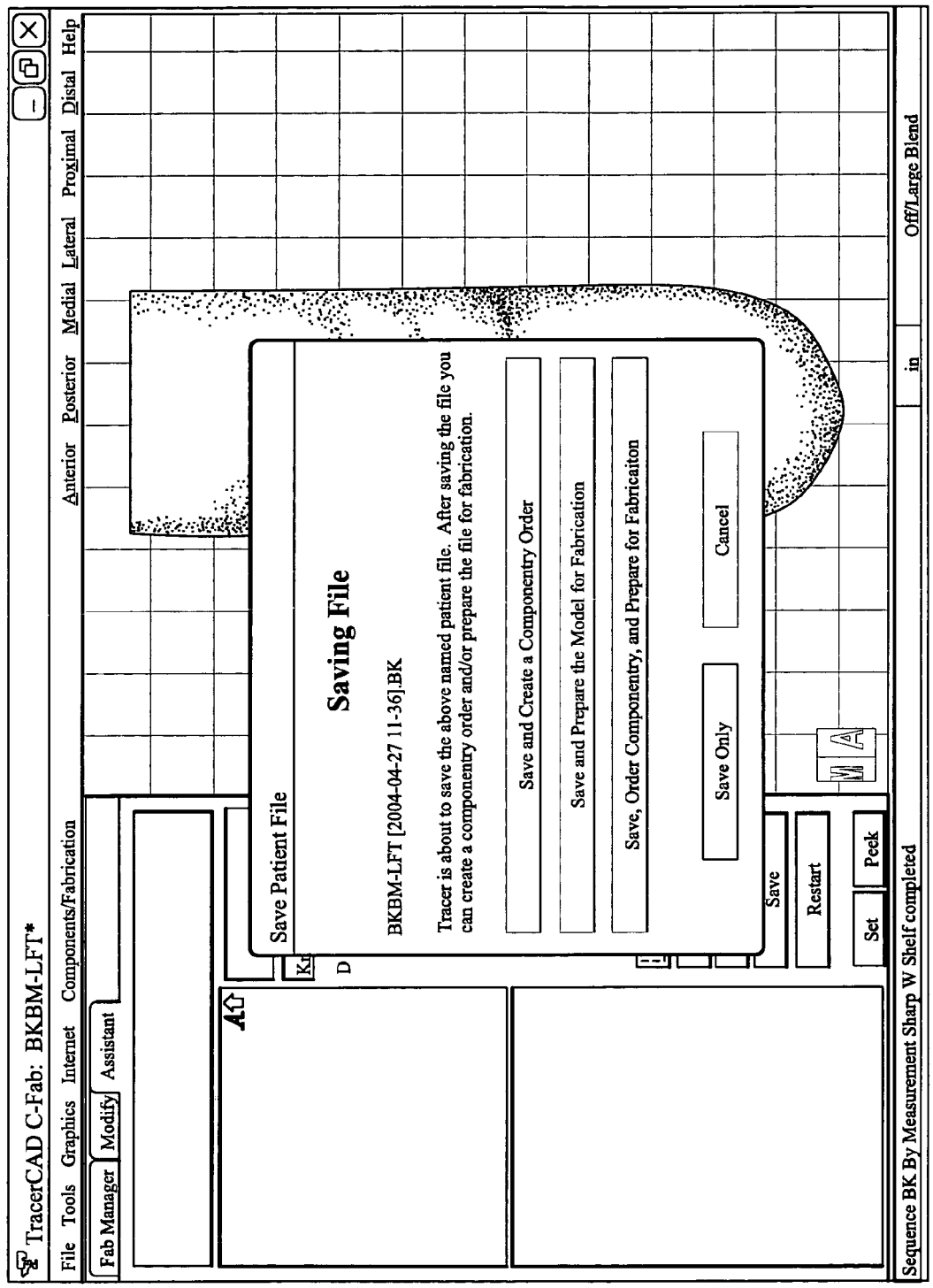
FIG. 23 is an exemplary screenshot prompting a user to save the electronic representation of the below knee residual limb customized in accordance with the present invention.

Referring to FIGS. 1, 17, and 18, the user will be prompted by TracerCAD to define a number of anatomical landmarks corresponding to the location of the patient's residual limb. As discussed above, TracerCAD is utilized to construct a three-dimensional electronic representation of a patients' residual limb without necessitating use of a scanning or mapping device. It is important to note that the default model displayed by TracerCAD does not include any indication regarding the location of landmarks chosen in accordance with principles of the present invention. The first landmark identified on the electronic representation, commonly referred to as the reference landmark, provides the initial point of reference from which all other landmarks will be identified and marked on the electronic limb model.

In this exemplary embodiment, the knee center will be the reference landmark. A user of TracerCAD defines the location of a plurality of landmarks on the template model using the location of the knee center as well as the measurements recorded in FIG. 1. The exemplary sequence, "BK by Measurement with Sharp W Shelf," prompts the user to mark the location of the landmarks in series that include, without limitation, patella tendon bar, tibia tubercle, fibula head, apex of gastrocs, distal tibia, interosseous groove, medial flare, level of shelf, medial condyle, and later condyle.

After the knee center is marked on the template model, the user will locate the patella tendon bar using the measurement as shown in FIG. 1 of KC (knee center) to MPT (medial patella tendon). By clicking on the mouse when at the location on the model where the patella tendon bar is located, the user marks the model with a "+" sign and an associated text identifier, "Mid Patella Tendon." Location of the tibia tubercle is analogously carried out using the measurement as shown in FIG. 1 of KC to Tib. Tuber (Tibia Tubercle). Likewise, the fibula head is located by selecting the "lateral view" and marking at a location posterior to the midline of the model that is level with the tibia tubercle. Similarly, the apex of gastrocs is located in the "anterior view" using the measurement as shown in FIG. 1 of KC to Apex of Gastrocs. The distal tibia is also located using the measurements of FIG. 1 and, in particular, the measurement of KC to Distal Tibia. Similarly to the procedures discussed above, marks are associated with locations on the model corresponding to the interosseous groove, the medial flare, the medial condyle, and the lateral condyle. After the marks have been associated with the model, TracerCAD prompts the user to advance so that the model is automatically adjusted based upon the information inputted in response to the sequence queries.

Referencing FIGS. 19-23, a user may further modify the model by using TracerCAD's Build and Blend tools. The sequence prompts the user to optionally build up areas, draw areas, or carve areas corresponding to a particular mark on the model, commonly referred to as "defining an area." After an area is defined, the user may then utilize TracerCAD's Blend tool to smooth the edges of the defined areas and eliminate stepwise changes in height along the surface of the model.

For instance, the user may carve a patella tendon bar within the model having an exemplary width of 2-3" and an exemplary length of 0.5-1". Thereafter, the patella tendon bar may be blended. The user advances to the next area after the preceding area has been defined and blended. Additional exemplary areas include, without limitation, the distal tibia, the interosseous groove, the medial flare, the fibula head, the level of shelf, the medial condyle, and the lateral condyle. After the requisite areas have been defined and blended, the user is prompted to save the current electronic model (See FIG. 23). The user may also recheck the model to ensure that the proper knee center to distal measurement is correct (See FIG. 13) prior to fabrication of the three-dimensional positive form of the patient's residual limb.

It is within the scope of the present invention that any of the above steps may be performed at the remote facility 102; and, further, that any of the above steps after the measurements are taken may be performed at the central fabrication facility 100. At some point, BK by Measurement data will need to be transmitted from the remote facility 102 to the central fabrication facility 100.

The central fabrication facility 100 may use the electronic model to fabricate a positive form of the patient's residual limb. Those of ordinary skill are familiar with the many techniques available for fabricating a positive form using an electronic model of a patient's residual limb. Likewise, those of ordinary skill are familiar with the many techniques available for fabricating a prosthetic socket using a positive form indicative of the patient's residual limb and/or using an electronic model of a patient's residual limb. After fabrication of the prosthetic socket, the socket is forwarded to the clinician for fitting and any minor adjustments that may be necessary to provide a comfortable, secure fit between the limb and socket. An exemplary method is discussed below.

Figure 2:
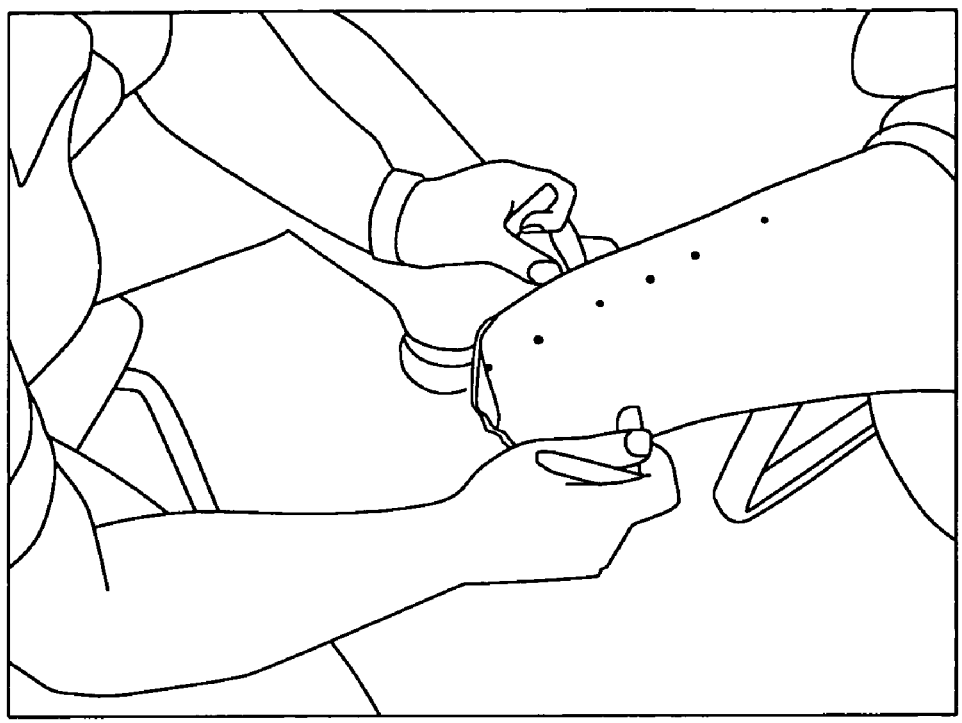
FIG. 2 is an exemplary photograph showing exemplary marks, corresponding to landmarks on an amputee's residual limb, in accordance with the present invention.
Figure 26:
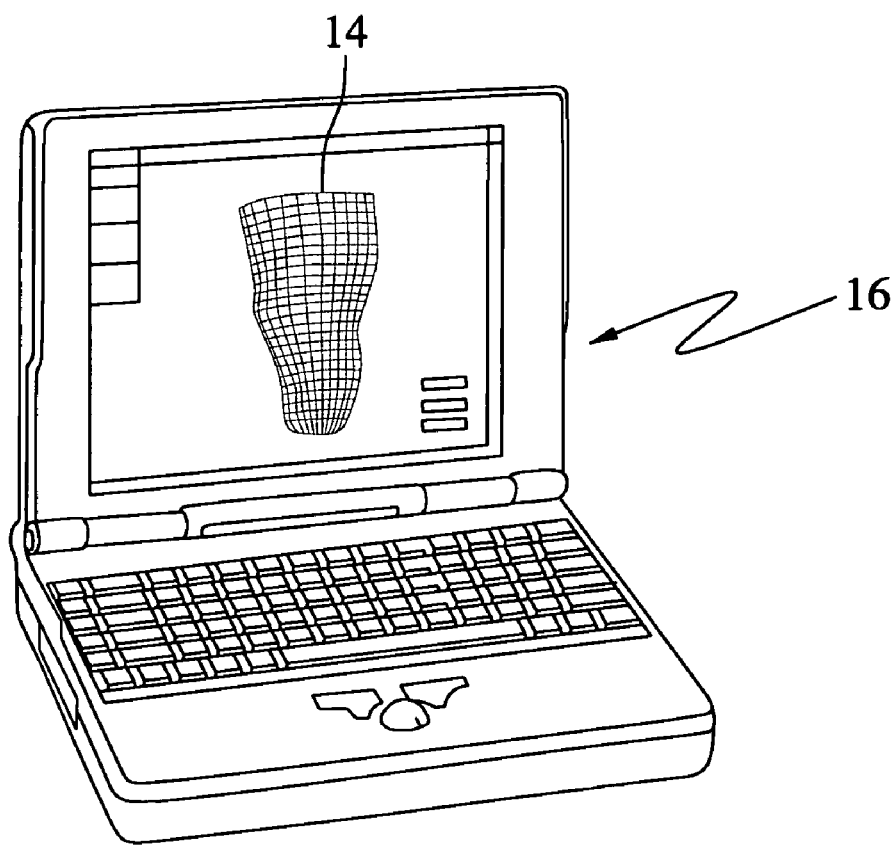
FIG. 26 is an exemplary CAD system for use with the present invention.
Figure 27:
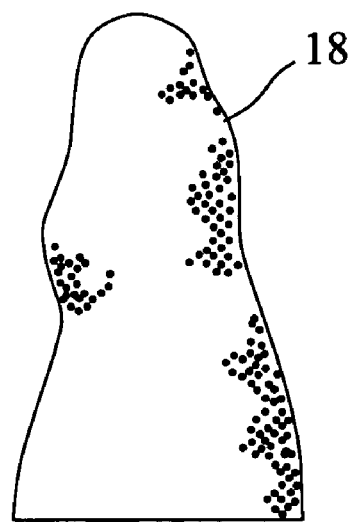
FIG. 27 is a perspective side view of a positive cast of a patient's residual limb.

As shown in FIGS. 26 and 27, such profile data may be represented in the form of a digital representation 14 as stored in a computerized design tool, depicted in FIG. 26 as a laptop CAD system 16. In addition to the BK by Measurement process described above, there are also several other known methods for obtaining the digital representation 14 of the patient's residual limb as depicted in FIG. 2. For example, such methods include the use of wand-based CAD systems such as the TracerCAD system, commercially available from Tracer Corporation of Miami, Fla., or by a digitizing system such as the Benz CAD/CAM and Digitizing systems, available through Benz Group Limited, Horns Cross, Greenhithe, Kent U.K. Such CAD systems are also capable of making the modifications to the digital representation of the limb based upon the skeletal and muscular positions in the patient's limb such that a finished prosthetic limb does not bear upon the distal end of the residual limb but rather on the areas around the residual limb.

It should be apparent to those of ordinary skill that such residual limb dimensions and modification data may be obtained and measured by other ways.

Referring back to FIGS. 24 and 25, the exemplary method may include the step 20 of generating a prosthetic device record for the patient on a computer memory 104 located at the central fabrication facility 100. In this exemplary method, the method includes the step 22 of associating the electronic representation (residual limb dimensions and modification data) of the patient's residual limb with the prosthetic device record stored on the computer memory 104. An exemplary prosthetic device record may also include patient name and contact information, prosthetist name and contact information, date of receipt of the fabrication instructions, the prosthetic device to be fabricated, expected or required completion date for fabricating the prosthetic device, and shipping or special handling instructions. The method also includes a step 25 of associating a unique identifier (such as a serial number, patient ID or the like) with the prosthetic device and storing that unique identifier in the patient's prosthetic device record. It is anticipated that the prosthetic device record will be stored in an electronic/digital database or in the computer memory 104, and may be optionally supplemented by a paper copy of such record. Nonetheless, the storage medium selected for the prosthetic record is one of preference and does not necessarily require utilization of an electronic/digital medium.

A later step in the process is the step 27 of fabricating the prosthetic component using the residual limb and modification data stored in the patient's record; and, during fabrication, applying the unique identifier on the prosthetic component, preferably in a permanent debossed fashion as described in detail below.

Figure 28:
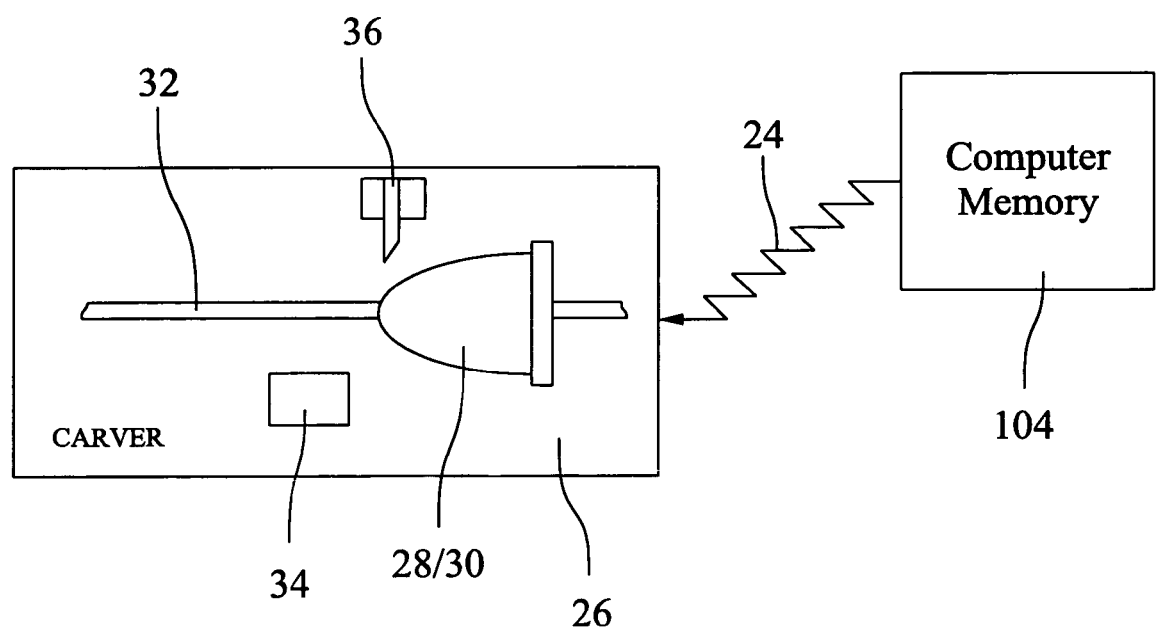
FIG. 28 is a schematic block diagram representation of the CAD tool and CNC milling machine for use with the present invention.

FIGS. 28-31 illustrate an exemplary implementation of step 27. As shown in FIG. 28, at the central fabrication facility 100, the residual limb and modification data is sent from the patient's record on the computer memory 104, via a data link 24, to a computer-numerically-controlled ("CNC") milling machine 26 to carry out the step of fabricating a positive device 28, in exemplary form, a socket mold 28. An appropriate CNC milling machine for use with the present invention is a "Benz Carver 1" available from Benz Group Limited, Horns Cross, Greenhithe, Kent, U.K. Upon receiving the dimensions of the modified digital representation of the patient's residual limb, the CNC milling machine 26 will use the dimensions to carve a positive socket mold from a carving blank 30. The carving blank 30 is fixed to a rotating shaft 32, and the internal control system 34 of the milling machine controls the radial and axial movement of a carving tool 36 with respect to the carving blank 30. The carving blank 30 can be a plaster, urethane foam or any other type of material suitable for the uses described herein. Suitable carving blanks for use with the present invention are commercially available through Prosthetic Design, Inc., Clayton, Ohio.

Figure 29:
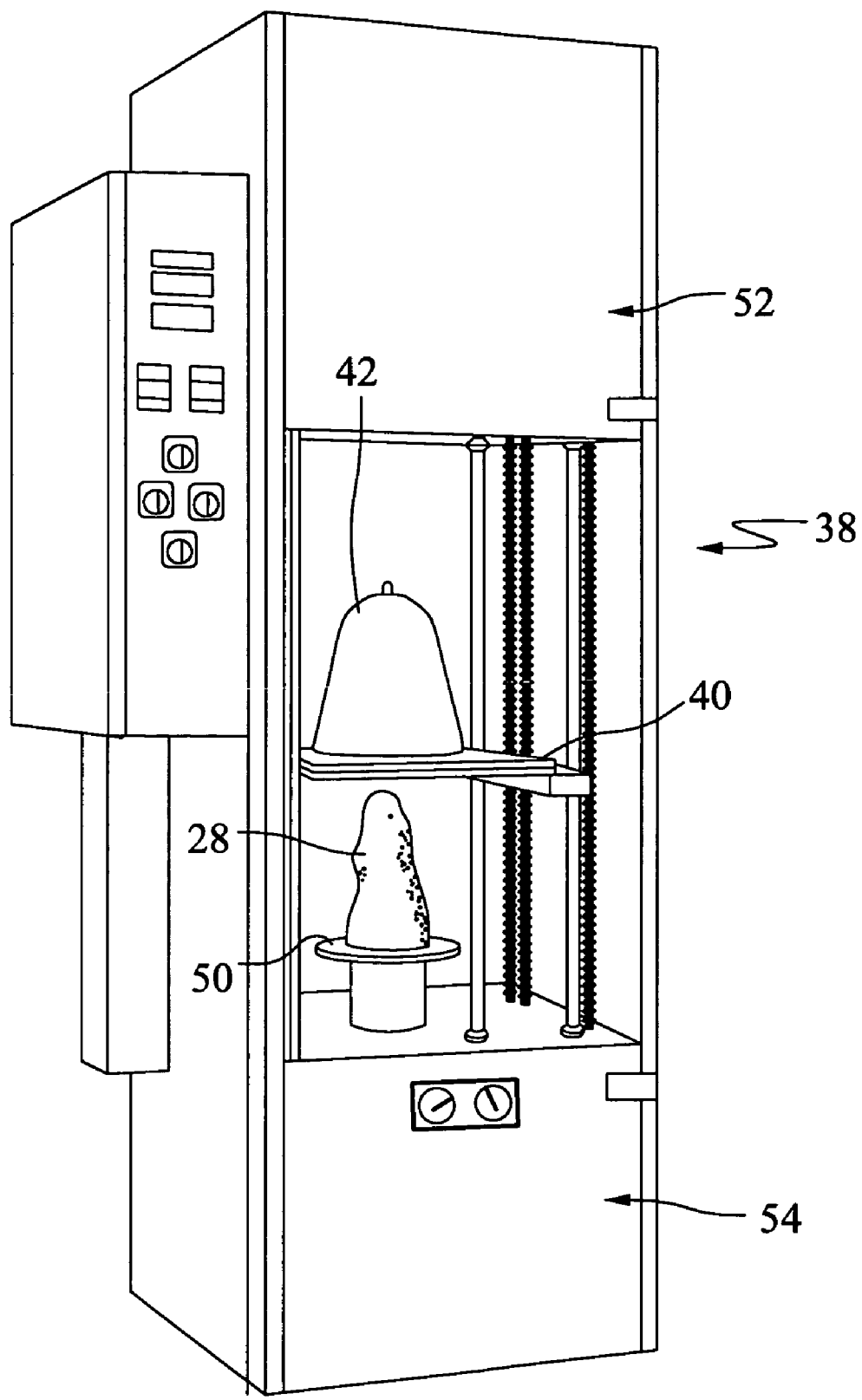
FIG. 29 is a perspective view of a socket manufacturing unit for use with the present invention.

As shown in FIG. 29, once the positive socket mold 28 has been created, either by hand or by the automated milling operations discussed above, the positive mold 28 is taken to a socket manufacturing unit ("SMU") 38 for forming a thermoplastic socket 39 (See FIG. 31) thereabout. A suitable SMU for use with the present invention is commercially available through Prosthetic Design, Inc., Clayton, Ohio. A typical SMU 38 will include a vertically translatable platform 40 for mounting a thermoplastic preform cone 42 thereto.

Figure 30:
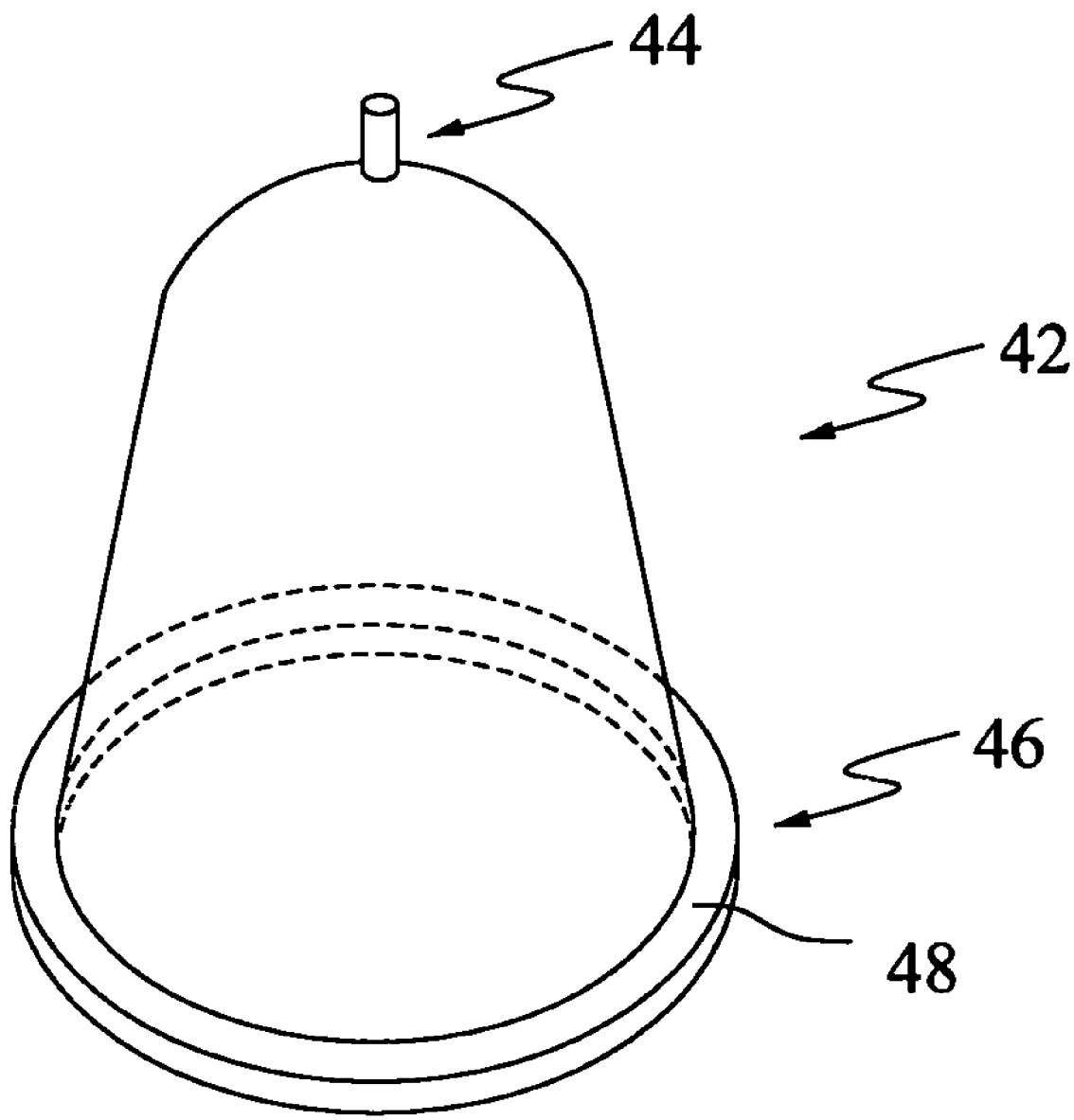
FIG. 30 is an exemplary preform cone for use with the present invention.

As shown in FIG. 30, a typical preform cone 42 is a hollow cone with a rounded distal end 44 and an open proximate end 46. The circumference of the preform cone generally increases with the distance from the distal end 44. A flange 48 extends radially outward from the proximate end 46 and facilitates mounting to the translatable platform 40 of the SMU. Exemplary preform cones 42 may be formed from a clear thermoplastic material, a polypropylene polymer material, a polypropylene homopolymer material, or a flexible thermoplastic material. The cones 42 are available in sizes that will typically range from 16 cm base diameter to 25 cm base diameter and are commercially available through Prosthetic Design, Inc., Clayton, Ohio.

Referring again to FIG. 29, the positive mold 28 will be mounted to a suction seat 50, which is positioned below the platform 40 such that the positive mold 28 is in vertical alignment with the preform cone 42. The platform 40 is lifted such that the preform cone 42 enters a heating chamber 52 at the top of the SMU, and is heated for a sufficient amount of time for the preform cone to become soft and pliable. Once sufficiently soft and pliable, the heated preform cone 42 is lowered by the platform 40 until the heated preform cone stretches over the positive mold 28 and suction seat 50. Next, a seal is formed between the heated preform cone 42, the positive mold 28, and the suction seat 50, where a vacuum pump (not shown) positioned within the vacuum chamber 54 creates a vacuum between the heated preform cone 42, the positive mold 28, and the suction seat 50, and in turn, causes the preform cone 42 to conform to the positive mold 28. Once the material of the preform cone 42 has cooled and sufficiently solidified, the positive mold 28 is extracted from the solidified material.

Alternatively, the socket 39 can be a laminated socket rather than a thermoplastic socket. The process for fabricating laminated sockets is known to persons skilled in the art and generally includes wrapping strips of resin-soaked fabric around a mold to form the socket. The resin is allowed to cure to form a rigid socket 39.

Referencing FIG. 31, the extended portion 56 of the socket 39 is debossed to include a unique indicia 120 for later association with the patient's record in the computer memory 104. In an exemplary form, the unique indicia 120 may include the prosthetic user's last name 122 followed by a first initial 124; an identification of the data type (BKBM-R is "Below Knee By Measurement-Right") 126; and a supplier or manufacturer identifier 128. For date of production purposes, the unique indicia 120 may also include day, month, and year 130. In a further detailed exemplary embodiment, the actual time the prosthetic article was produced in hours and possibly minutes and seconds may also be added to the unique indicia 120. For example, an exemplary prosthetic socket may be fabricated at 11:30 am and a corresponding "11.30" may be included as part of the unique indicia 120.

An exemplary process for creating the unique indicia 120 includes the steps of debossing a thin metallic strip, such as an aluminum labeling strip (Office Depot #710-472-144), with an embossing machine and transferring a debossed impression to the prosthetic socket using the embossed strip. An exemplary embossing machine includes the Imperial Regal electric nameplate machine. Using such exemplary tools, it is possible to emboss letters, numerals, and symbols onto the metallic strip. The positive side of the strip (embossed side), identified by the raised letters, numerals, (dimensioned to receive a cylindrical shuttle lock therein) and/or symbols in relation to surrounding areas, is pushed into the extended portion 56 at the distal end of the socket 39 while the socket material is capable of sustaining an impression using the metallic strip (i.e., while the plastic is still hot). The metallic strip is then removed resulting in a series of debossed grooves being created within the surface of the extended portion 56 corresponding to letters, numerals, and/or any symbols embossed onto the metallic strip.

A coloring agent may be added to the debossed grooves to provide contrast between the letters, numerals, and/or any symbols and the surrounding areas of the socket 39. The coloring agent may be selected to provide the maximum contrast between the indicia 120 and the remainder of the socket 39. The extended portion 56 was chosen as the desired portion of the socket 39 to receive this debossed indicia 120 because the shape and dimensions of this portion will be substantially the same for each patient. Of course, it is within the scope of the invention to apply the indicia 120 to other portions of the socket 39.

Figure 31:
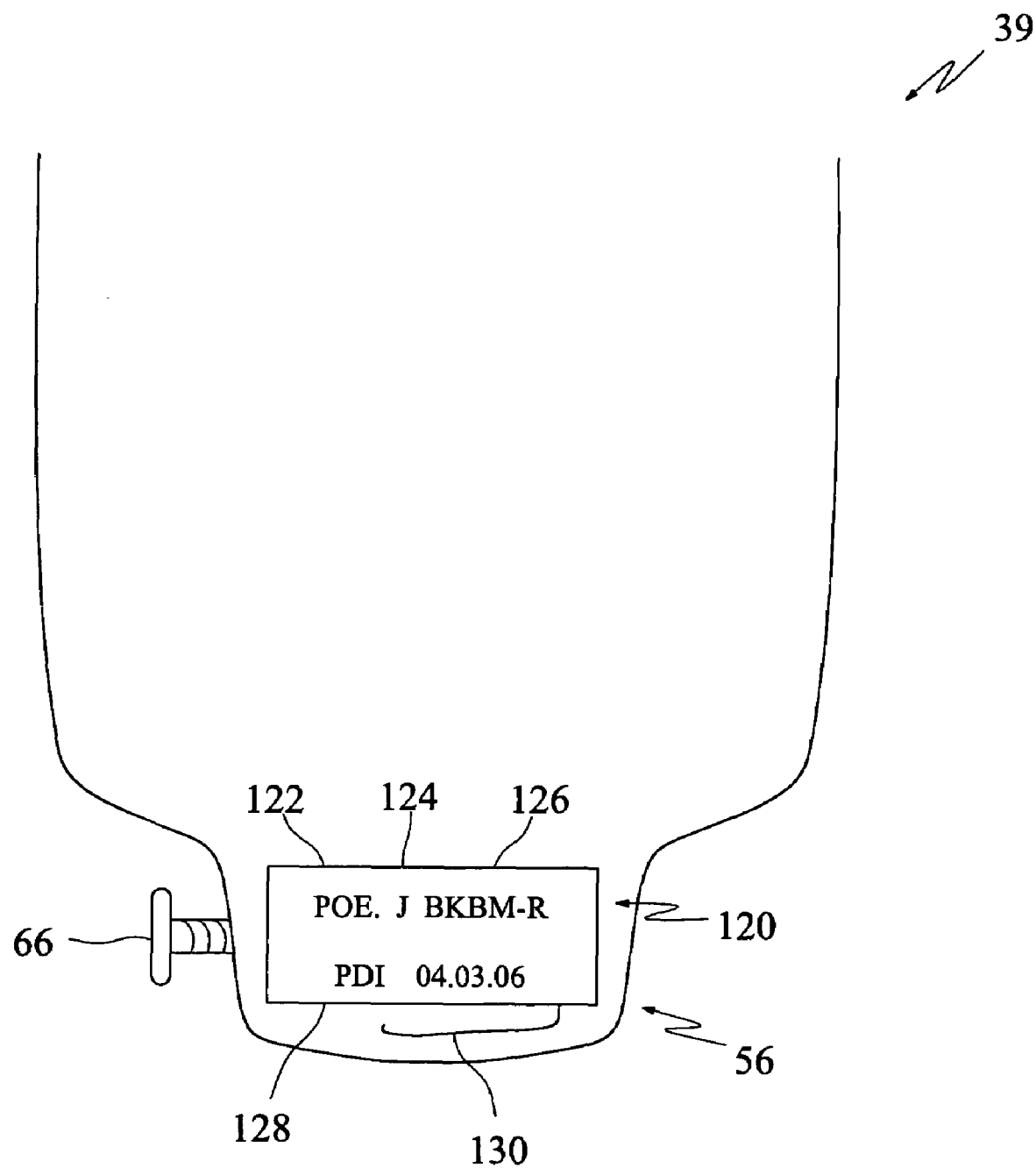
FIG. 31 is a frontal view of an exemplary prosthetic socket fabricated in accordance with the present invention.

Referencing FIG. 31, after the socket 39 has sufficiently solidified, any excess material is removed from the socket 39 and the proximate surfaces are then smoothed leaving a finished socket 39. Once the socket 39 has been fabricated, the remaining portions of the patient's prosthetic limb can be assembled thereto. The distal end of the socket 39 may include an extended portion 56 to which a shuttle lock 66 is releasably mounted thereto. The extended portion 56 may also include a distal orifice adapted to be generally aligned with the orifice in the shuttle lock 66 to secure additional prosthetic components to the socket 39.

It is also within the scope of the invention to generate indicia 120 on the socket 39 using other available mechanisms, such as by using, for example, a milling machine, etching machine or laser to engrave (or otherwise mark) the indicia 120 on the socket 39. Some of these mechanisms can be used to mark the indicia either a solidified or un-solidified socket depending upon the mechanisms used.

Referring back to FIGS. 24 and 25, following the fabricating and marking step 27, is the step 60 of updating, if necessary, information in the patient's prosthetic device record. At this point the prosthetic component is shipped to the appropriate remote office 102 for fitting onto the patient by the prosthetist. Any adjustments and final assembly of the prosthetic limb are then performed.

If, at a later time, the prosthetic component needs to be replaced (i.e., due to wear or failure) or if the patient wishes to have another prosthetic limb fabricated for any reason, the patient merely needs to visit any of the remote offices 102, which will transmit some or all of the unique identifier 120 along with appropriate instructions to the central fabrication facility 100. The central fabrication facility 100 will refabricate the prosthetic component identified by the unique identifier and ship it back to the ordering remote office. Thus, the present invention includes the step 62 of receiving fabrication instructions by the central fabrication facility 100 for fabricating a unique prosthetic component, such as a socket 39, based upon receiving fabrication instructions and one or more pieces of information associated with the unique indicia 120. In this manner, the present invention may include the step 64 of retrieving the prosthetic device record in the computer memory by searching for or by cross-referencing a particular unique indicia 120. In such an exemplary circumstance, the prosthetic device 39 may be fabricated again in step 27 using the measurements and other data associated with the retrieved prosthetic device record 120.

Following from the above description and invention summaries, it should be apparent to those of ordinary skill in the art that, while the methods and apparatuses herein described constitute exemplary embodiments of the present invention, it is to be understood that the inventions contained herein are not limited to the above precise embodiment and that changes may be made without departing from the scope of the invention as defined by the following proposed points of novelty. Likewise, it is to be understood that it is not necessary to meet any or all of the identified advantages or objects of the invention disclosed herein in order to fall within the scope of the invention, since inherent and/or unforeseen advantages of the present invention may exist even though they may not have been explicitly discussed herein.

What is claimed is:

1. A method of fabricating a prosthetic socket for a residual limb of an amputee, the method comprising the steps of:
   (a) identifying a series of landmarks on the residual limb of the amputee;
   (b) manually measuring the residual limb using the series of landmarks as points of reference to generate measurement data in relation to certain of the landmarks;
   (c) inputting the measurement data into a software tool based upon the manual measurements taken from the residual limb in step (b);
   (d) correlating, with the assistance of the software tool, the measurement data with a three-dimensional template of a residual limb to generate a three dimensional electronic representation of the residual limb of the amputee;
   (e) designating at least one point on the three-dimensional electronic representation of the residual limb taken from the group consisting of: of knee center, mid patella tendon, tibial tuberosity, distal tibia, patella tendon bar, medial flare, interosseous groove, apex of gastrocs, fibula head, lateral condyle, and medial condyle;
   (f) customizing, with the assistance of the software tool, and with reference to the at least one point the three-dimensional electronic representation, wherein the customizing step includes a step taken from a group consisting of: (f1) building onto the three-dimensional electronic representation, (f2) removing from the three-dimensional electronic representation, (f3) smoothing a surface of the three-dimensional electronic representation, and (f4) adding to the volume of the three-dimensional electronic representation to account for one or more prosthetic limb components to be positioned within a prosthetic limb socket fabricated from the three-dimensional electronic representation
   (g) manufacturing a physical three dimensional representation of the residual limb of the amputee using the customized three-dimensional electronic representation;
   (h) molding a material at least partially over the physical three dimensional representation of the residual limb to form a prosthetic socket;
   (i) embossing a unique indicia onto a transfer substrate; and
   (j) debossing the unique indicia onto a prosthetic component by impressing the transfer substrate into the prosthetic component;
   wherein the unique indicia includes at least one of: a name corresponding to the prosthetic recipient, a manufacturer indicia; an approximate date of manufacture of the prosthetic component; an approximate time of manufacture of the prosthetic component, and a device identifier.

2. A method for fabricating a prosthetic limb socket component of a prosthetic limb assembly, comprising the steps of:
   collecting dimensional information pertaining to a patient's residual limb;
   generating outer surface dimension information of a positive mold of a socket component to be worn on the patient's residual limb utilizing at least a portion of the dimensional information pertaining to the patient's residual limb;
   storing the outer surface dimension information in an electronic storage location associated with the patient;
   generating a unique indicia linked with at least one of the patient, the dimension information and the electronic storage location; and
   forming a first positive mold utilizing the outer surface dimension information;

fabricating a first prosthetic limb socket component over the first positive mold; and marking the first prosthetic limb socket component with the unique indicia.

3. The method of claim 2, further comprising the step of fabricating a second, duplicate prosthetic limb socket component, which includes the steps of:

accessing the dimension information from the electronic storage location using the unique indicia marked on the first prosthetic limb socket component;

forming a second positive mold utilizing the accessed dimension information; and fabricating a second prosthetic limb socket component over the second positive mold.

4. The method of claim 2, wherein the fabricating step includes a step of molding a heated thermoplastic cone over the first positive mold.

5. The method of claim 2, wherein the fabricating step includes a step of layering resin-impregnated fabric over the first positive mold.

* * * * *